United States Patent
Chu et al.

(10) Patent No.: US 12,263,292 B2
(45) Date of Patent: Apr. 1, 2025

(54) DAMPENING ELEMENT FOR FLUID MANAGEMENT SYSTEM

(71) Applicant: BOSTON SCIENTIFIC SCIMED, INC., Maple Grove, MN (US)

(72) Inventors: Michael S. H. Chu, Brookline, MA (US); Mayur kiran Patel, Framingham, MA (US); Sacha Tang, Lowell, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 972 days.

(21) Appl. No.: 16/719,011

(22) Filed: Dec. 18, 2019

(65) Prior Publication Data
US 2020/0200313 A1 Jun. 25, 2020

Related U.S. Application Data

(60) Provisional application No. 62/782,124, filed on Dec. 19, 2018.

(51) Int. Cl.
*A61M 1/00* (2006.01)
*A61M 5/168* (2006.01)
(Continued)

(52) U.S. Cl.
CPC ............. *A61M 1/772* (2021.05); *F16L 55/04* (2013.01); *A61M 1/30* (2013.01); *A61M 1/3604* (2014.02);
(Continued)

(58) Field of Classification Search
CPC ............ G01L 19/0609; G05D 16/0402; G05D 16/0404; Y10T 137/7924; Y10T 137/7925
(Continued)

(56) References Cited

U.S. PATENT DOCUMENTS 563,192 A * 6/1896 De Laval .................. F15B 1/08
  138/31
2,353,692 A * 7/1944 Cunningham ........... F24F 11/30
  91/460
(Continued)

FOREIGN PATENT DOCUMENTS

CN 104870035 A 8/2015
CN 105451790 A 3/2016
(Continued)

OTHER PUBLICATIONS

International Search Report and Written Opinion dated Apr. 7, 2020 for International Application No. PCT/US2019/067145.

*Primary Examiner* — Robert K Arundale
*Assistant Examiner* — Richard K. Durden
(74) *Attorney, Agent, or Firm* — Seager, Tufte & Wickhem, LLP

(57) ABSTRACT

A fluid management system may include a fluid pump capable of generating a pulsatile flow of fluid, a fluid pathway for transporting the pulsatile flow of fluid from a fluid source through the fluid pump to a medical device, a dampening element in fluid communication with the fluid pathway and operably independent of the fluid pump, the dampening element comprising one or more barrels, each barrel including a movable seal member disposed within the barrel and a biasing member disposed within the barrel and engaged with the movable seal member, the dampening element being responsive to pressure fluctuations of the pulsatile fluid flow to actively dampen the pressure fluctuations, and a fluid flow sensor disposed along the fluid pathway between the dampening element and the medical device to measure a flow rate of the smoothened pulsatile fluid flow in both flow directions.

20 Claims, 16 Drawing Sheets

(51) Int. Cl.
   *F04B 11/00* (2006.01)
   *F16L 55/04* (2006.01)
   *A61M 1/30* (2006.01)
   *A61M 1/36* (2006.01)
   *F04B 39/00* (2006.01)
   *F15B 1/02* (2006.01)

(52) U.S. Cl.
   CPC . *A61M 5/16886* (2013.01); *A61M 2205/3334* (2013.01); *A61M 2206/22* (2013.01); *F04B 11/0008* (2013.01); *F04B 11/0016* (2013.01); *F04B 11/0033* (2013.01); *F04B 39/0027* (2013.01); *F15B 1/021* (2013.01)

(58) Field of Classification Search
   USPC .................................................... 138/30, 31
   See application file for complete search history.

(56) References Cited

U.S. PATENT DOCUMENTS

| | | | |
|---|---|---|---|
| 2,355,001 A * | 8/1944 | Longenecker | F16L 55/05 138/31 |
| 2,474,512 A | 6/1949 | Bechtold et al. | |
| 2,591,528 A * | 4/1952 | Filstrup, Jr. | F16K 17/10 137/538 |
| 2,592,613 A * | 4/1952 | Snyder | F16L 55/052 138/31 |
| 2,638,932 A * | 5/1953 | Alexander | F15B 1/106 138/30 |
| 2,700,488 A * | 1/1955 | Rafferty | B67D 7/763 137/493.5 |
| 2,721,446 A * | 10/1955 | Bumb | F15B 1/24 60/415 |
| 2,753,892 A * | 7/1956 | Deardorff | F16J 15/004 277/910 |
| 2,789,581 A * | 4/1957 | Kerr | F15B 1/04 138/31 |
| 2,884,955 A * | 5/1959 | Yost | F16L 55/052 138/31 |
| 3,006,364 A * | 10/1961 | Osborn | F16L 55/052 137/538 |
| 3,075,558 A * | 1/1963 | Von Forell | F16L 55/052 138/30 |
| 3,467,140 A * | 9/1969 | Hanson | F16J 15/48 138/31 |
| 3,741,692 A * | 6/1973 | Rupp | F16L 55/053 417/540 |
| 3,804,125 A * | 4/1974 | Sonneman | F16L 55/053 138/30 |
| 3,818,934 A * | 6/1974 | Borsanyi | A61M 60/894 435/284.1 |
| 4,392,791 A | 7/1983 | Mandroian | |
| 4,444,198 A | 4/1984 | Petre | |
| 4,648,866 A * | 3/1987 | Malbrancq | A61M 1/3603 210/90 |
| 4,650,462 A | 3/1987 | DeSatnick et al. | |
| 4,657,529 A * | 4/1987 | Prince | A61M 1/303 604/6.11 |
| 4,741,678 A | 5/1988 | Nehring | |
| 4,826,482 A | 5/1989 | Kamen | |
| 4,834,630 A | 5/1989 | Godwin | |
| 4,921,477 A | 5/1990 | Davis | |
| 4,935,005 A | 6/1990 | Haines | |
| 4,997,347 A | 3/1991 | Roos | |
| 4,998,914 A | 3/1991 | Wiest et al. | |
| 5,018,547 A * | 5/1991 | Alcorn | B01F 25/315 137/538 |
| 5,152,746 A | 10/1992 | Atkinson et al. | |
| 5,257,917 A | 11/1993 | Minarik et al. | |
| 5,520,638 A | 5/1996 | O'Quinn et al. | |
| 5,598,869 A * | 2/1997 | Nelson | G05D 16/0404 137/557 |
| 5,868,168 A | 2/1999 | Mott et al. | |
| 5,871,478 A | 2/1999 | Berrigan | |
| 6,024,720 A | 2/2000 | Chandler et al. | |
| 6,149,621 A | 11/2000 | Makihara | |
| 6,159,160 A | 12/2000 | Hsei et al. | |
| 6,209,583 B1 * | 4/2001 | Mohr | F15B 1/103 220/721 |
| 6,283,937 B1 * | 9/2001 | Takamatsu | A61M 1/74 604/31 |
| 6,396,583 B1 | 5/2002 | Clare | |
| 6,551,080 B2 | 4/2003 | Andersen et al. | |
| 6,595,957 B1 | 7/2003 | Griffiths et al. | |
| 6,669,455 B2 * | 12/2003 | Welch | F04B 43/06 417/540 |
| 6,939,111 B2 | 9/2005 | Huitt et al. | |
| 7,645,127 B2 | 1/2010 | Hagen et al. | |
| 7,678,070 B2 | 3/2010 | Kumar et al. | |
| 7,798,017 B2 | 9/2010 | Betz | |
| 8,087,909 B2 | 1/2012 | Shener | |
| 8,100,022 B2 | 1/2012 | Choisnet | |
| 8,167,592 B2 | 5/2012 | Shener-Irmakoglu | |
| 8,187,466 B2 | 5/2012 | Folden et al. | |
| 8,226,549 B2 | 7/2012 | Kumar et al. | |
| 8,308,726 B2 | 11/2012 | Kumar et al. | |
| 8,348,844 B2 * | 1/2013 | Kunjan | A61B 5/15003 600/366 |
| 8,366,667 B2 | 2/2013 | Chan et al. | |
| 8,388,570 B2 | 3/2013 | Kumar et al. | |
| 8,449,500 B2 | 5/2013 | DelCastillo et al. | |
| 8,512,283 B2 | 8/2013 | Kumar et al. | |
| 8,591,464 B2 | 11/2013 | Kumar et al. | |
| 8,667,990 B2 * | 3/2014 | Becker | F16F 9/065 251/59 |
| 8,790,096 B2 | 7/2014 | Sorensen | |
| 8,876,489 B2 | 11/2014 | Shener | |
| 9,028,398 B2 | 5/2015 | Kumar et al. | |
| 9,482,216 B2 | 11/2016 | Sorenson | |
| 9,603,990 B2 | 3/2017 | Woolford | |
| 9,889,246 B2 | 2/2018 | Woolford | |
| 2005/0163637 A1 | 7/2005 | Chang et al. | |
| 2006/0122557 A1 * | 6/2006 | Kumar | A61M 3/0212 604/67 |
| 2007/0258829 A1 * | 11/2007 | Oude Vrielink | F04B 43/1276 417/46 |
| 2008/0308168 A1 * | 12/2008 | O'Brien, II | F15B 1/24 138/31 |
| 2009/0131859 A1 * | 5/2009 | DelCastillo | A61M 5/16831 604/65 |
| 2009/0157040 A1 * | 6/2009 | Jacobson | A61M 5/16804 604/505 |
| 2009/0217993 A1 * | 9/2009 | Easley | B01L 3/502746 428/166 |
| 2010/0137802 A1 * | 6/2010 | Yodfat | A61M 5/14248 604/152 |
| 2011/0139285 A1 * | 6/2011 | Lundberg | F16L 55/053 138/30 |
| 2013/0108482 A1 | 5/2013 | Johnson | |
| 2013/0310743 A1 * | 11/2013 | Yagi | A61M 5/16836 604/111 |
| 2015/0025311 A1 | 1/2015 | Kadan et al. | |
| 2015/0267854 A1 * | 9/2015 | Selwyn | F15B 1/08 138/30 |
| 2016/0025085 A1 * | 1/2016 | Hay | F04B 11/0008 417/472 |
| 2016/0123320 A1 | 5/2016 | Tsoukalis | |
| 2020/0191336 A1 * | 6/2020 | Critsinelis | G05D 16/2013 |

FOREIGN PATENT DOCUMENTS

| | | |
|---|---|---|
| EP | 1010437 A1 | 6/2000 |
| WO | 89003230 A1 | 4/1989 |
| WO | 91006325 A1 | 5/1991 |
| WO | 2006021873 A2 | 3/2006 |
| WO | 2010129128 A1 | 11/2010 |
| WO | 2017168409 A1 | 10/2017 |

* cited by examiner

DAMPENING ELEMENT FOR FLUID MANAGEMENT SYSTEM

CROSS-REFERENCE TO RELATED APPLICATIONS

This application claims the benefit of priority under 35 U.S.C. § 119 of U.S. Provisional Application No. 62/782,124 filed Dec. 19, 2018, the entire disclosure of which is hereby incorporated by reference.

TECHNICAL FIELD

The disclosure relates generally to medical devices, systems, and/or methods for dampening pressure fluctuations within a medical fluid management system.

BACKGROUND

In some fluid management systems, peristaltic or membrane pumps may be used which cause a pulsatile or non-continuous flow of fluid into (infusion) and/or out of (suction) a medical device and/or a body cavity or lumen. Peristaltic or membrane pumps may have certain desirable qualities depending upon the procedure being performed. However, the pressure fluctuations that result from the use of peristaltic or membrane pumps may be undesirable in some situations. There is an ongoing need to provide alternative components of fluid management systems to reduce pressure fluctuations of an inflow of fluid and/or an outflow of fluid through the fluid management system.

SUMMARY

In a first aspect, a fluid management system may comprise a fluid pump capable of generating a pulsatile flow of fluid; a fluid pathway for transporting the pulsatile flow of fluid from a fluid source through the fluid pump to a medical device; a dampening element in fluid communication with the fluid pathway, the dampening element comprising one or more barrels, each barrel including a movable seal member disposed within the barrel and a biasing member disposed within the barrel and engaged with the movable seal member, the dampening element being responsive to pressure fluctuations of the pulsatile fluid flow to actively dampen the pressure fluctuations and smoothen the pulsatile fluid flow; and a fluid flow sensor disposed along the fluid pathway between the dampening element and the medical device to measure a flow rate of the smoothened pulsatile fluid flow in both flow directions of the fluid pathway.

In addition or alternatively, the dampening element may be capable of actively dampening the pressure fluctuations in both flow directions.

In addition or alternatively, the biasing member may be an elastic element.

In addition or alternatively, the elastic element may be a spring.

In addition or alternatively, the elastic element may be in compression.

In addition or alternatively, the elastic element may be in tension.

In addition or alternatively, the biasing member may be a gas, such as a gas at atmospheric pressure (e.g., atmospheric air) or a compressed gas.

In addition or alternatively, the biasing member may be a vacuum or a partial vacuum.

In addition or alternatively, the movable seal member may include at least one sealing element extending around a perimeter of the movable seal member.

In addition or alternatively, the fluid management system may further comprise a pressure relief port.

In addition or alternatively, the pressure relief port may be opened by axial translation of the movable seal member.

In addition or alternatively, each barrel may include an adjustable cap configured to adjust a working length of its barrel.

In addition or alternatively, each adjustable cap may threadably engage its respective barrel.

In addition or alternatively, a fluid management system may comprise a fluid pump capable of generating a pulsatile flow of fluid; a fluid pathway for transporting the pulsatile flow of fluid from a fluid source through the fluid pump to a medical device; a dampening element in fluid communication with the fluid pathway, the dampening element comprising a first barrel and a second barrel, the dampening element being responsive to pressure fluctuations of the pulsatile fluid flow to actively dampen the pressure fluctuations and smoothen the pulsatile fluid flow. The first barrel may include a first movable seal member disposed within the first barrel and a first biasing member disposed within the first barrel and engaged with the first movable seal member. The second barrel may include a second movable seal member disposed within the second barrel and a second biasing member disposed within the second barrel and engaged with the second movable seal member.

In addition or alternatively, the first barrel dampens the pulsatile fluid flow in a distal direction.

In addition or alternatively, the second barrel dampens the pulsatile fluid flow in a proximal direction.

In addition or alternatively, the first barrel may be independent of the second barrel.

In addition or alternatively, the first barrel and the second barrel may be formed within a single monolithic structure.

In addition or alternatively, a fluid management system may comprise a fluid pump capable of generating a pulsatile flow of fluid; a fluid pathway for transporting the pulsatile flow of fluid from a fluid source through the fluid pump to a medical device; a dampening element in fluid communication with the fluid pathway, the dampening element comprising a first barrel and a second barrel, the dampening element being responsive to pressure fluctuations of the pulsatile fluid flow to actively dampen the pressure fluctuations and smoothen the pulsatile fluid flow; and a fluid flow sensor disposed along the fluid pathway between the dampening element and the medical device to measure a flow rate of the pulsatile fluid flow in both flow directions of the fluid pathway. The first barrel may include a first movable seal member disposed within the first barrel and a first biasing member disposed within the first barrel and engaged with the first movable seal member, the first barrel being configured to dampen the pressure fluctuations in a distal direction. The second barrel may include a second movable seal member disposed within the second barrel and a second biasing member disposed within the second barrel and engaged with the second movable seal member, the second barrel being configured to dampen the pressure fluctuations in a proximal direction. The first barrel and the second barrel may both be positioned between the fluid pump and the fluid flow sensor.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
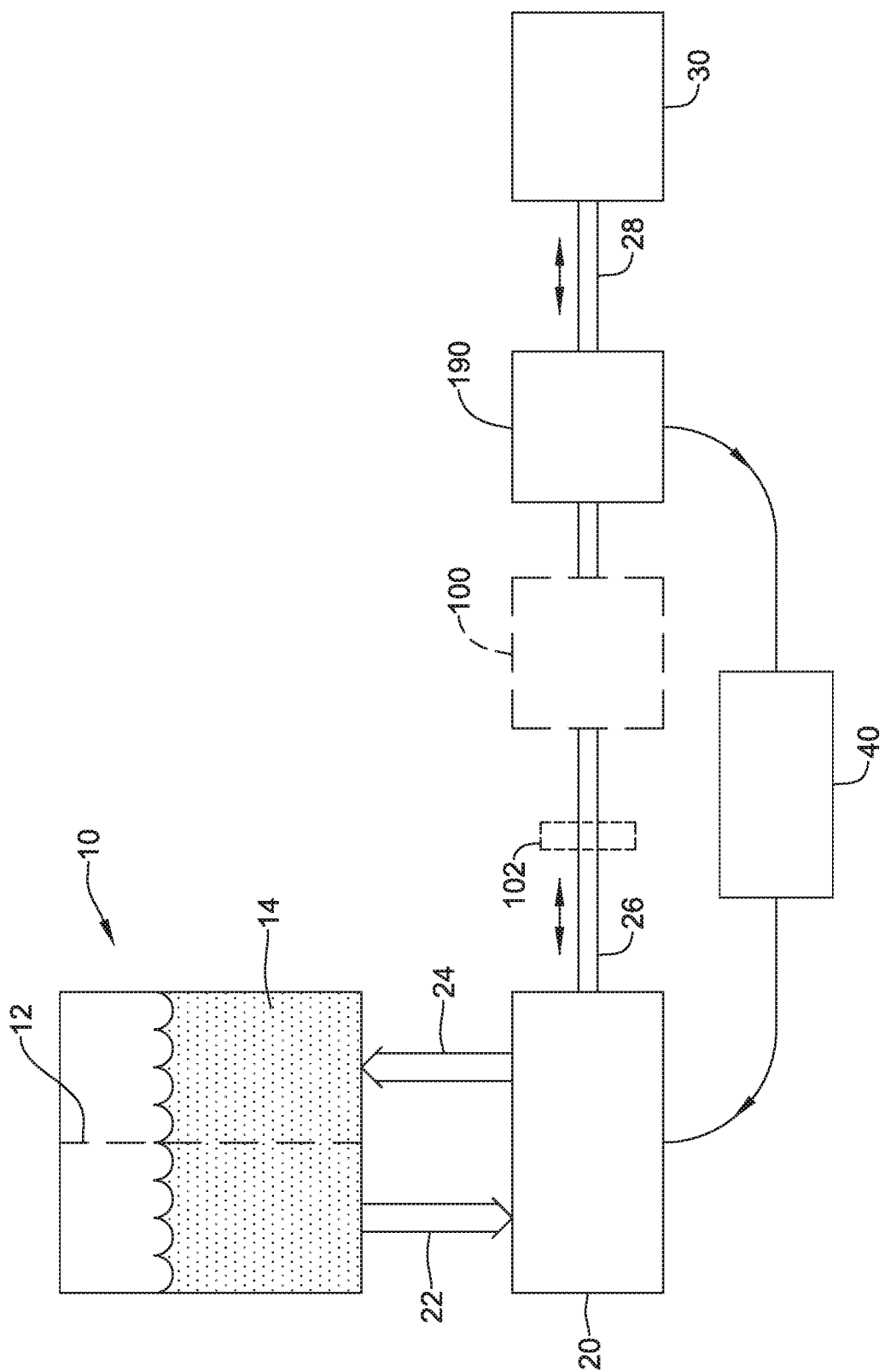
FIG. 1 is a schematic view of a fluid management system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified. As such, in any given figure, some features may not be shown, or may be shown schematically, for simplicity. Additional details regarding some components, configurations, and/or embodiments may be illustrated in other figures in greater detail.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below.

However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

FIG. 1 is a schematic view of a fluid management system. The fluid management system may include a fluid reservoir, such as a fluid source 10. The fluid source 10 may include a filtering element 12 sized and configured to filter impurities, debris, or other unwanted elements from a fluid 14 so that filtered fluid 14 may be recirculated through the fluid management system. In some instances, the filtering element 12 may be located in the fluid reservoir to filter fluid returning to the reservoir. In other instances, the filtering element 12 may be arranged in the fluid pathway of fluid returning to the fluid source 10. The fluid management system may include a fluid pump 20 capable of generating a non-continuous or pulsatile flow of fluid. In some instances, the fluid pump 20 may be a roller or peristaltic pump, or a membrane pump, for example. In at least some embodiments, the fluid pump 20 may be capable of generating a pulsatile flow of fluid in both a distal direction (i.e., fluid inflow from the pump to a patient) and a proximal direction (i.e., fluid outflow from a patient to the pump). In some embodiments, the fluid management system may include a fluid pathway for transporting the pulsatile flow of fluid from the fluid source 10 through the fluid pump 20 to a medical device 30, such as an endoscope, a tissue resection device, etc. In some embodiments, the fluid pathway may include an inflow or infusion line 22 disposed between the fluid source 10 and/or the filtered fluid and the fluid pump 20. The infusion line 22 may be configured for single-direction and/or flow of fluid in a distal direction (e.g., infusion, positive pressure, etc.) from the fluid source 10 to the fluid pump 20. In some embodiments, the infusion line 22 may include a one-way valve configured to prevent retrograde or proximal flow of fluid back toward and/or into the fluid source 10. In some embodiments, the one-way valve may be disposed within the infusion line 22, at a proximal end or a distal end of the infusion line 22, within the fluid source 10, and/or within the fluid pump 20. In some embodiments, the fluid pathway may include an outflow or return line 24 disposed between the fluid source 10 and the fluid pump 20. The return line 24 may be configured for single-direction and/or flow of fluid in a proximal direction (e.g., suction, negative pressure, etc.) from the fluid pump 20 to the fluid source 10. In some embodiments, the return line 24 may include a one-way valve configured to prevent distal flow of fluid back toward and/or into the fluid pump 20. In some embodiments, the one-way valve may be disposed within the return line 24, at a proximal end or a distal end of the return line 24, within the fluid source 10, and/or within the fluid pump 20.

In some embodiments, the fluid pathway may include a first segment 26 disposed between the fluid pump 20 and a dampening element 100 disposed between the fluid pump 20 and the medical device 30. The first segment 26 of the fluid pathway may be configured for fluid flow in both the distal direction and the proximal direction depending on the control of the fluid pump 20, such as the rotational direction of the fluid pump 20. The fluid pathway may include a second segment 28 disposed between the dampening element 100 and the medical device 30. The second segment 28 of the fluid pathway may be configured for fluid flow in both the distal direction and the proximal direction depending on the control of the fluid pump 20, such as the rotational direction of the fluid pump 20. In some embodiments, additional segments may be included between individual elements and/or structures of the fluid management system. In some embodiments, the fluid pathway may optionally include a connector 102 configured to attach, couple, and/or assemble various elements of the fluid management system. The connector 102 (and/or multiple connectors 102) may permit the addition of and/or the interchangeability of multiple elements of the fluid management system. For example, the dampening element 100 may be attached, coupled, and/or assembled to the first segment 26 of the fluid pathway with a first connector 102 disposed therebetween. Similarly, a second connector 102 (e.g., FIGS. 3-15) may be disposed between the dampening element 100 and the second segment 28 of the fluid pathway. In some embodiments, the dampening element 100 may include the first connector 102 and/or the second connector 102. For example, in some embodiments, the connector 102 (the first and/or the second connector(s) 102 discussed above) may be incorporated into and/or monolithically formed with the dampening element 100 such that lengths of tubing, defining the fluid pathways from the dampening element 100, may be attached to the dampening element 100 and extend therefrom. Other arrangements and/or configurations are also contemplated.

In some embodiments, the fluid management system may include a fluid flow sensor 190 disposed along the fluid pathway between the dampening element 100 and the medical device 30 to measure a flow rate of the pulsatile fluid flow in the distal direction (i.e. fluid inflow), in the proximal direction (i.e., fluid outflow), and/or in both flow directions (e.g., in the distal direction and the proximal direction). In one example, there is a single fluid pathway which carries flow in both the distal direction and the proximal direction, and the fluid flow sensor 190 is capable of measuring the flow rate of the pulsatile fluid flow in either flow direction or in both flow directions of the fluid pathway. Other arrangements and/or configurations are also contemplated.

In some embodiments, the fluid management system may include a controller 40. The controller 40 may be operatively connected to and/or in communication with the fluid flow sensor 190 and the fluid pump 20. The fluid flow sensor 190 may output a signal to the controller 40 indicative of the flow rate of the pulsatile fluid flow through the second segment 28 of the fluid pathway. The controller 40 may be configured to adjust and/or control the fluid pump 20 in order to adjust and/or control the pulsatile fluid flow to a desired flow rate. In some embodiments, if the flow rate of the pulsatile fluid flow is outside of a predetermined range, the controller 40 may stop the fluid pump 20 and/or terminate the pulsatile fluid flow.

In some embodiments, the fluid management system may include one or more, or a plurality of pressure sensors in the fluid pathway for measuring the pressure of the fluid therein. The pressure sensor(s) may output a signal to the controller 40 indicative of the pressure of the pulsatile fluid flow through the fluid pathway. The controller 40 may be configured to adjust and/or control the fluid pump 20 in order to adjust and/or control the pulsatile fluid flow based on the sensed fluid pressure. In some embodiments, if the pressure of the pulsatile fluid flow is outside of a predetermined range, the controller 40 may stop the fluid pump 20 and/or terminate the pulsatile fluid flow.

In some instances the fluid pump 20 and the controller 40 may be capital equipment intended for multiple uses, whereas the dampening element 100, flow sensor 190 and associated tubing forming the fluid pathway may be part of a disposable tubing set intended to be disposed of after use. Thus, a new tubing set, including a new dampening element 100, flow sensor 190 and associated tubing may be used for each medical procedure, while the fluid pump 20 and controller 40 are reused.

Figure 2A:
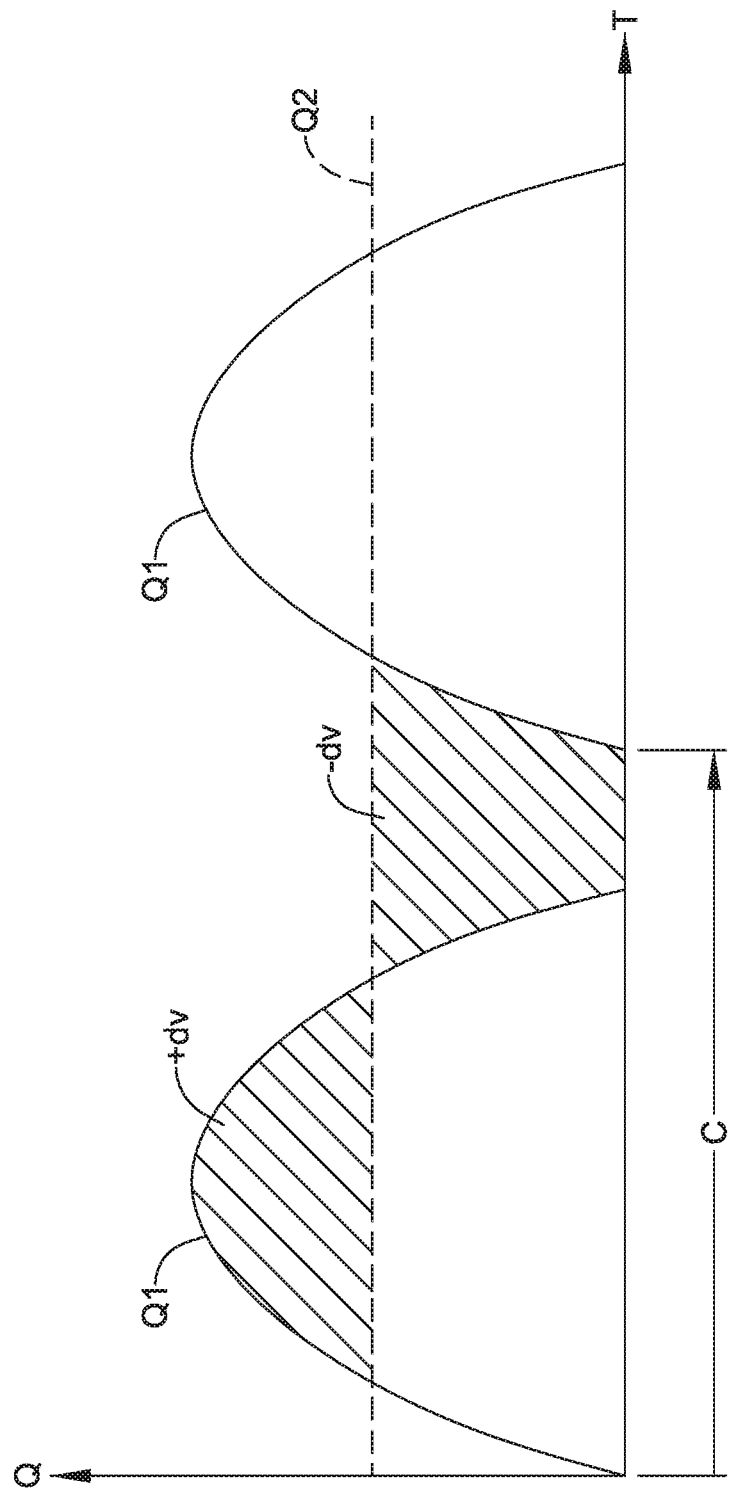
FIG. 2A is a schematic illustration of fluid pressure fluctuations in a positive pulsatile flow of fluid.

FIG. 2A illustrates a graph of positive fluid flow Q (e.g., infusion) versus time T over one cycle of the fluid pump 20 with and without the dampening element 100. Without the dampening element 100, the graph has a pronounced curve showing fluctuations in fluid pressure and/or fluid flow through the cycle. A pulsatile pressure cycle C may have positive and negative slopes indicated by the solid line Q1—which represents flow without the dampening element 100. The pulsatile pressure cycle C, if undampened, causes the fluid flow rate to increase above and fall below the dotted line Q2—which represents desired smoothened flow with the dampening element 100. With the dampening element 100 in place, a portion of the fluid volume (+dv) is "stored" within the dampening element 100, as will be discussed herein, as the flow rate rises above the dotted line Q2, thereby limiting the flow rate past the dampening element 100 to the dotted line Q2. The stored fluid volume (+dv) may be returned to the fluid flow when the pulsatile pressure cycle C decreases below the dotted line Q2, which would otherwise create a negative volume (−dv), if not dampened by the dampening element 100. The use of the dampening element 100 allows the "stored" fluid volume (+dv) to be "given back" to the fluid pathway and negate the negative volume (−dv) to smoothen the flow rate at or near the desired flow rate represented by the dotted line Q2. Accordingly, the dampening element 100 permits the fluid flow Q to be maintained at a more consistent level with pressure and/or fluid flow fluctuations that are reduced in quantity and/or magnitude.

When a positive pressure pulse (e.g., distal flow) is created during infusion, fluid enters one or more barrels of the dampening element 100, displacing fluid volume within the one or more barrels to move a movable seal member and/or a biasing member, thereby storing fluid to compensate for the positive volume (+dv) with respect to the desired flow Q2. When the positive pulsatile fluid pressure and/or flow decreases below the desired flow Q2, the biasing member of the dampening element 100 pushes fluid out of the one or more barrels of the dampening element 100 and back into the fluid pathway, thereby releasing stored fluid to compensate for the negative volume (−dv) with respect to the desired flow Q2. The discharge will create a smoother and/or steady fluid flow at the fluid flow sensor 190 downstream of the dampening element 100. The biasing member (via the movable seal member) responds to an increased state of the pulsatile fluid flow in the fluid pathway by deflecting and permitting the movable seal member to move away from its initial state or position, and later returns the movable seal member to its initial state or position in a decreased state of the pulsatile fluid flow in the fluid pathway.

Figure 2B:
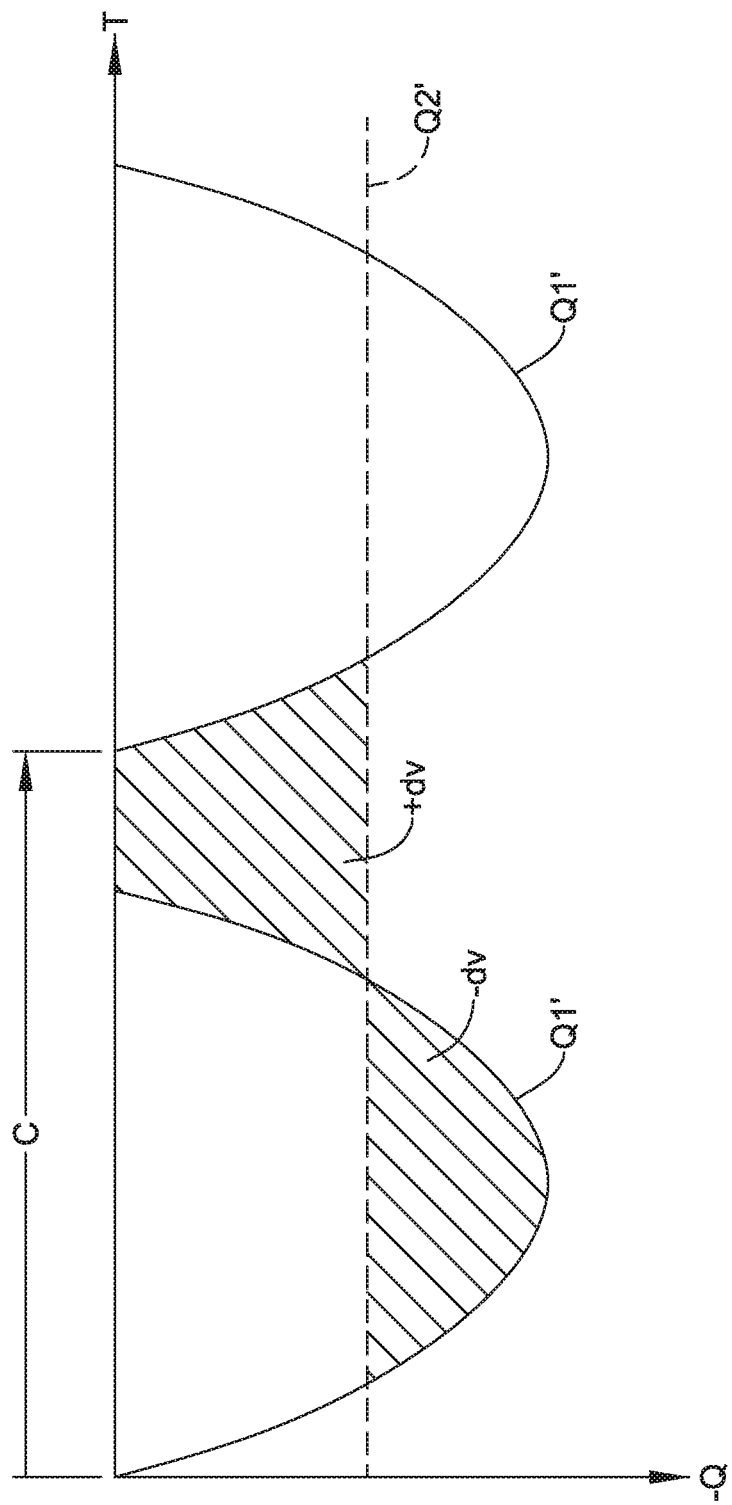
FIG. 2B is a schematic illustration of fluid pressure fluctuations in a negative pulsatile flow of fluid.

FIG. 2B illustrates a graph of negative fluid flow Q (e.g., suction) versus time T over one cycle of the fluid pump 20 with and without the dampening element 100. Without the dampening element 100, the graph has a pronounced curve showing fluctuations in fluid pressure and/or fluid flow through the cycle. A pulsatile pressure cycle C may have negative and positive slopes indicated by the solid line Q1'—which represents flow without the dampening element 100. The pulsatile pressure cycle C, if undampened, causes the fluid flow rate to increase above and fall below the dotted line Q2'—which represents desired smoothened flow with the dampening element 100. With the dampening element 100 in place, a portion of the fluid volume (+dv) is "stored" within the dampening element 100, as will be discussed herein, as the flow rate rises above the dotted line Q2' and then returned to the fluid flow when the pulsatile pressure cycle C decreases below the dotted line Q2', which would otherwise create a negative volume (−dv). The dampening element 100 may be configured to release a portion of the stored fluid volume into the fluid flow path to compensate for the negative fluid volume (−dv) with respect to the desired flow Q2', thereby maintaining the flow rate distal of the dampening element 100 to the dotted line Q2'. With the dampening element 100 in place, a portion of the fluid volume (+dv) is "stored" within the dampening element 100, and then allow the "stored" fluid volume (+dv) to be "given back" or released to the fluid pathway to offset and/or compensate for the negative volume (−dv) to smoothen the flow rate at or near the desired flow rate represented by the dotted line Q2'. Accordingly, the dampening element 100 permits the fluid flow Q to be maintained at a more consistent level with pressure and/or fluid flow fluctuations that are reduced in quantity and/or magnitude.

When the negative pulsatile fluid pressure and/or flow increases (e.g., the negative slope) during aspiration or suction (e.g., proximal flow), fluid is drawn out of one or more barrels of the dampening element 100 and back into the fluid pathway, thereby releasing stored fluid to compensate for the negative volume (−dv) with respect to the desired flow Q2'. The release will create a smoother and/or steady fluid flow at the fluid flow sensor 190 downstream of the dampening element 100. When a negative pressure pulse (e.g., proximal flow) during aspiration or suction subsides (e.g., negative pressure diminishes), fluid enters the one or more barrels of the dampening element 100, filling the fluid volume within the one or more barrels as a biasing member displaces a movable seal member away from the fluid pathway, thereby storing fluid to later compensate for the negative volume (−dv) with respect to the desired flow Q2' as negative pressure increases. The biasing member (via the movable seal member) responds to a decreased state of the negative pulsatile fluid flow in the fluid pathway by urging the movable seal member to move away from the fluid pathway, and later permits the movable seal member to be drawn toward the fluid pathway in an increased state of the pulsatile fluid flow in the fluid pathway.

The dampening element 100 may be capable of actively dampening the pressure fluctuations of the pulsatile fluid flow in the distal direction (e.g., inflow or infusion), in the proximal direction (e.g., outflow or aspiration), and/or in both flow directions (e.g., in the distal direction and the proximal direction), depending upon the configuration of the dampening element 100 used.

Figure 3:
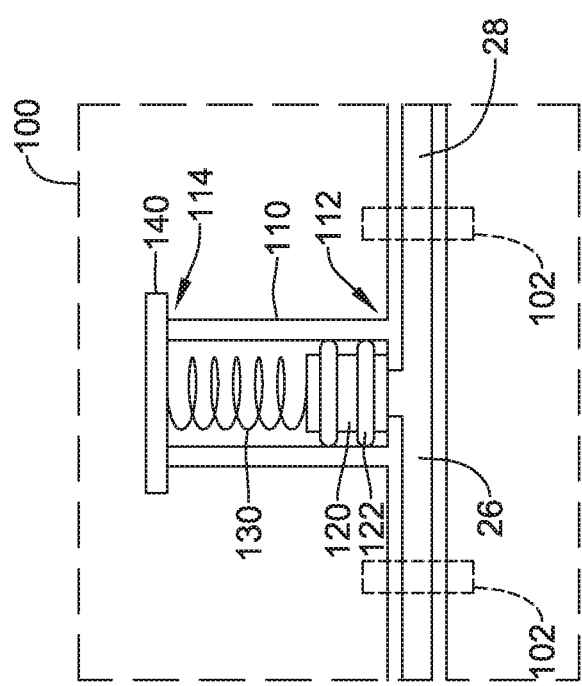
FIGS. 3-9 illustrate selected aspects of example dampening elements.

FIG. 3 illustrates a partial cross-sectional view of one example of the dampening element 100. The dampening element 100 may be positioned and/or disposed between the first segment 26 of the fluid pathway and the second segment 28 of the fluid pathway. The dampening element 100 may be in fluid communication with the fluid pathway, and in some instances the dampening element 100 may be provided as a disposable tubing set with tubing extending from the dampening element 100 defining the first segment 26 and/or the second segment 28, which may be removably engaged with the fluid pump 20 for moving fluid therethrough. The dampening element 100 may comprise one or more chambers, such as cylinders or barrels 110 having an opening or port (such as a single opening or port) in fluid communication with the fluid pathway, each barrel 110 including a movable seal member 120 disposed within the barrel 110 (and/or a lumen defined by an inner surface of the barrel 110), a biasing member 130 disposed within the barrel 110 (and/or the lumen defined by the barrel 110) and engaged with the movable seal member 120, and a cap 140 secured to the barrel 110 opposite the fluid pathway. The lumen of the barrel 110 may be a cylindrical lumen with the movable seal member 120 sealingly engaged with the cylindrical inner surface defining the lumen. The cap 140 may be selectively lockable onto the barrel 110 and/or removable from the barrel. As mentioned above, in some embodiments, the dampening element 100 may include the first connector 102 and/or the second connector 102 for connecting the dampening element 100 with tubing of the tubing set. In the example of FIG. 3, the first connector 102 may couple proximal tubing to the dampening element 100 and extend proximally therefrom to the pump 20 and the second connector 102 may couple distal tubing to the dampening element and extend distally therefrom to the medical device 30. Although the first connector 102 and the second connector 102 are illustrated, this is not intended to be limiting. Some suitable, but non-limiting, examples of materials for the dampening element 100, the one or more barrels 110, the movable seal member 120, the biasing member 130, and/or the cap 140 are discussed below.

In some embodiments, a first end 112 of each of the one or more barrels 110 (and/or each of the lumens defined by the one or more barrels 110) may include a port in fluid communication with the fluid pathway, and the cap 140 may be secured to an opposing second end 114 of the barrel 110 (and/or the lumen defined by the barrel 110). The movable seal member 120 may be disposed within the barrel 110 (and/or the lumen defined by the barrel 110) between the port leading to the fluid pathway and the cap 140. The movable seal member 120 may be configured to sealingly engage an inner surface and/or an inner wall of the barrel 110. In some embodiments, the movable seal member 120 may include at least one sealing element 122 extending around a perimeter of the movable seal member 120 and configured to sealingly engage the inner surface and/or the inner wall of the barrel 110. For example, in some embodiments, the at least one sealing element 122 may include at least one O-ring (e.g., one O-ring, two O-rings, three O-rings, etc.) extending around the movable seal member 120 and configured to sealingly engage the inner surface and/or the inner wall of the barrel 110. Some suitable, but non-limiting, examples of materials for the at least one sealing element 122 include but are not limited to thermoset elastomers, silicone rubbers, butyl rubbers, and/or polyisoprene.

The movable seal member 120 may be configured to translate axially within the one or more barrels 110 and/or within the lumen defined by the one or more barrels 110. In some embodiments, using two or more sealing elements 122 may help to prevent tilting, cocking, and/or wedging of the movable seal member 120 within the barrel 110 and/or the lumen defined by the barrel 110. The dampening element 100 may be configured to be responsive to pressure fluctuations of the pulsatile fluid flow to actively dampen the pressure fluctuations and smoothen the pulsatile fluid flow. In the example of FIG. 3, the biasing member 130 may be an elastic element. In some embodiments, the elastic element may be a spring (e.g., compression spring), a compressible member, or other similar structure or element. In the example of FIG. 3, the elastic element may be secured in compression or equilibrium within the barrel 110 between the movable seal member 120 and the cap 140. Accordingly, the dampening element 100 may be configured to actively dampen pressure fluctuations of the pulsatile fluid flow in the distal direction (e.g., positive flow; during infusion). The biasing member 130 may bias and/or urge the movable seal member 120 toward and/or into an initial position proximate the first end 112 or otherwise position the movable seal member 120 toward the first end 112. The movable seal member 120, in the initial position, may be at the first end 112 of the barrel 110 immediately adjacent to the port of the barrel 110 in fluid communication with the fluid pathway and/or the first segment 26 and/or the second segment 28.

As fluid flow and/or pressure increases, fluid may flow into the barrel 110 through the port and apply a force against the movable seal member 120, thereby urging the movable seal member 120 away from the fluid pathway and/or away from the initial position at the first end 112 and toward the second end 114 of the barrel 110 when the force exceeds the biasing force of the biasing member 130, and the biasing member 130 may be compressed. This permits a portion of the fluid volume to be stored within the one or more barrels 110 of the dampening element 100 to compensate for the positive volume (+dv), which results in a reduced peak pressure and/or flow rate through the fluid pathway downstream of the dampening element 100. The fluid volume that may be "stored" within the dampening element 100 may be calculated as the product of the cross-sectional area of the lumen of the barrel 110 and the axial displacement, length, or distance the movable seal member 120 is moved away from the initial position (e.g., $dv = A*L$). The biasing force exerted by the elastic element (e.g., the biasing member 130) may be calculated using Hooke's law (e.g., $F=-kx$; where k is the rate or spring constant and x is the displacement length of the elastic element from its equilibrium position).

In at least some embodiments wherein the biasing member 130 includes the elastic element, the cap 140 may include a vent fluidly connecting the interior of the barrel 110 (e.g., the lumen defined by the barrel 110) with outside atmosphere to prevent compressed gas from modifying or influencing the biasing force of the elastic element. For example, a portion of the barrel 110 and/or the lumen defined by the barrel 110 further defined by a side of the movable seal member 120 opposite the fluid pathway and/or the at least one sealing element 122 axially farthest away from the fluid pathway may be excluded from the fluid pathway and/or may not be fluidtight. Alternatively, in some embodiments, the cap 140 may include a seal member rendering the portion of the barrel 110 and/or the lumen defined by the barrel 110 further defined by the side of the movable seal member 120 opposite the fluid pathway and/or the at least one sealing element 122 axially farthest away from the fluid pathway fluidtight, and any trapped gas within the barrel 110 may add to the biasing force of the elastic element as the elastic element and the trapped gas within the barrel 110 are compressed by axial translation of the movable seal member 120 toward the second end 114.

Figure 4:
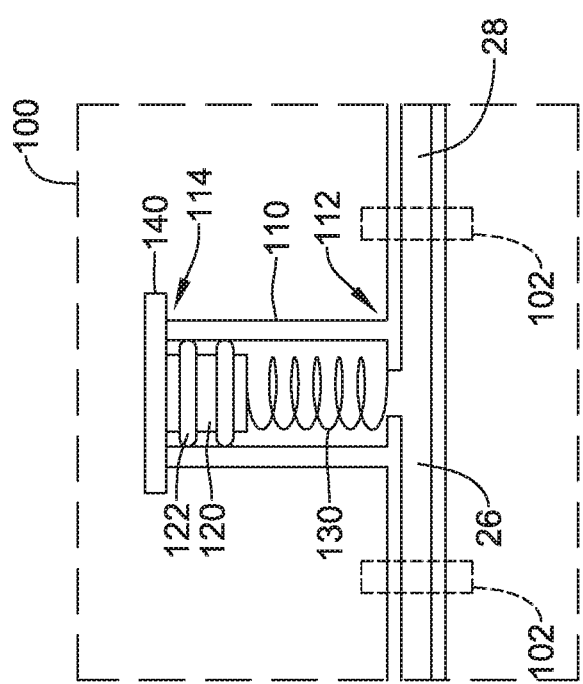

FIG. 4 illustrates a partial cross-sectional view of another example of the dampening element 100. The dampening element 100 may be positioned and/or disposed between the first segment 26 of the fluid pathway and the second segment 28 of the fluid pathway. The dampening element 100 may be in fluid communication with the fluid, and in some instances the dampening element 100 may be provided as a disposable tubing set with tubing extending from the dampening element 100 defining the first segment 26 and/or the second segment 28, which may be removably engaged with the fluid pump 20 for moving fluid therethrough. The dampening element 100 may comprise one or more chambers, such as cylinders or barrels 110 having an opening or port (such as a single opening or port) in fluid communication with the fluid pathway, each barrel 110 including a movable seal member 120 disposed within the barrel 110 (and/or a lumen defined by an inner surface of the barrel 110), a biasing member 130 disposed within the barrel 110 (and/or the lumen defined by the barrel 110) and engaged with the movable seal member 120, and a cap 140 secured to the barrel 110 opposite the fluid pathway. The lumen of the barrel 110 may be a cylindrical lumen with the movable seal member 120 sealingly engaged with the cylindrical inner surface defining the lumen. The cap 140 may be selectively lockable onto the barrel 110 and/or removable from the barrel. As mentioned above, in some embodiments, the dampening element 100 may include the first connector 102 and/or the second connector 102 for connecting the dampening element 100 with tubing of the tubing set. In the example of FIG. 4, the first connector 102 may couple proximal tubing to the dampening element 100 and extend proximally therefrom to the pump 20 and the second connector 102 may couple distal tubing to the dampening element and extend distally therefrom to the medical device 30. Although the first connector 102 and the second connector 102 are illustrated, this is not intended to be limiting. Some suitable, but non-limiting, examples of materials for the dampening element 100, the one or more barrels 110, the movable seal member 120, the biasing member 130, and/or the cap 140 are discussed below.

In some embodiments, the first end 112 of each of the one or more barrels 110 (and/or each of the lumens defined by the one or more barrels 110) may include a port in fluid communication with the fluid pathway, and the cap 140 may be secured to the opposing second end 114 of the barrel 110 (and/or the lumen defined by the barrel 110). The movable seal member 120 may be disposed within the barrel 110 (and/or the lumen defined by the barrel 110) between the port leading to the fluid pathway and the cap 140. The movable seal member 120 may be configured to sealingly engage the inner surface and/or the inner wall of the barrel 110. In some embodiments, the movable seal member 120 may include at least one sealing element 122 extending around the perimeter of the movable seal member 120 and configured to sealingly engage the inner surface and/or the inner wall of the barrel 110. For example, in some embodiments, the at least one sealing element 122 may include at least one O-ring (e.g., one O-ring, two O-rings, three O-rings, etc.) extending around the movable seal member 120 and configured to sealingly engage the inner surface and/or the inner wall of the barrel 110. Some suitable, but non-limiting, examples of materials for the at least one sealing element 122 include but are not limited to thermoset elastomers, silicone rubbers, butyl rubbers, and/or polyisoprene.

The movable seal member 120 may be configured to translate axially within the one or more barrels 110 and/or within the lumen defined by the one or more barrels 110. In some embodiments, using two or more sealing elements 122 may help to prevent tilting, cocking, and/or wedging of the movable seal member 120 within the barrel 110 and/or the lumen defined by the barrel 110. The dampening element 100 may be configured to be responsive to pressure fluctuations of the pulsatile fluid flow to actively dampen the pressure fluctuations and smoothen the pulsatile fluid flow. In the example of FIG. 4, the biasing member 130 may be an elastic element. In some embodiments, the elastic element may be a spring (e.g., compression spring), a compressible member, or other similar structure or element. In the example of FIG. 4, the elastic element may be secured in compression or equilibrium within the barrel 110 between the movable seal member 120 and first end 112 of the barrel 110. Accordingly, the dampening element 100 may be configured to actively dampen pressure fluctuations of the pulsatile fluid flow in the proximal direction (e.g., negative flow; during suction). The biasing member 130 may bias and/or urge the movable seal member 120 toward and/or into an initial position proximate the second end 114 or otherwise position the movable seal member 120 toward the second end 114. The movable seal member 120, in the initial position, may be at the second end 114 of the barrel 110 immediately adjacent to and/or in contact with the cap 140.

During pulsatile fluid flow in the distal direction (e.g., positive flow; during infusion) and/or during periods of low flow and low suction in the proximal direction (e.g., negative flow; during suction), fluid may flow into and/or be stored within the barrel 110 and/or the lumen defined by the barrel 110 between the first end 112 and the movable seal member 120. As the suction or negative pressure increases in magnitude to a point where the suctioning force exceeds the biasing force of the biasing member 130, fluid may be drawn out of the barrel 110, thereby "pulling" the movable seal member 120 away from the cap 140 and/or away from the initial position at the second end 114 and toward the first end 112 of the barrel 110, and the biasing member 130 may be compressed. This permits a portion of the fluid volume to be released from the one or more barrels 110 of the dampening element 100 to compensate for the negative volume (−dv), which results in a smoothened pressure and/or flow rate through the fluid pathway.

In at least some embodiments wherein the biasing member 130 includes the elastic element, the cap 140 may include a vent fluidly connecting the interior of the barrel 110 (e.g., the lumen defined by the barrel 110) with outside atmosphere to prevent compressed gas from modifying or influencing the biasing force of the elastic element. For example, the portion of the barrel 110 and/or the lumen defined by the barrel 110 further defined by the side of the movable seal member 120 opposite the fluid pathway and/or the at least one sealing element 122 axially farthest away from the fluid pathway may be excluded from the fluid pathway and/or may not be fluidtight. Alternatively, in some embodiments, the cap 140 may include a seal member rendering the portion of the barrel 110 and/or the lumen defined by the barrel 110 further defined by the side of the movable seal member 120 opposite the fluid pathway and/or the at least one sealing element 122 axially farthest away from the fluid pathway fluidtight, and any gas (or lack thereof) trapped within the barrel 110 may add to the biasing force of the elastic element as the elastic element and the trapped gas within the barrel 110 is expanded and/or subjected to vacuum by axial translation of the movable seal member 120 toward the first end 112.

Figure 5:
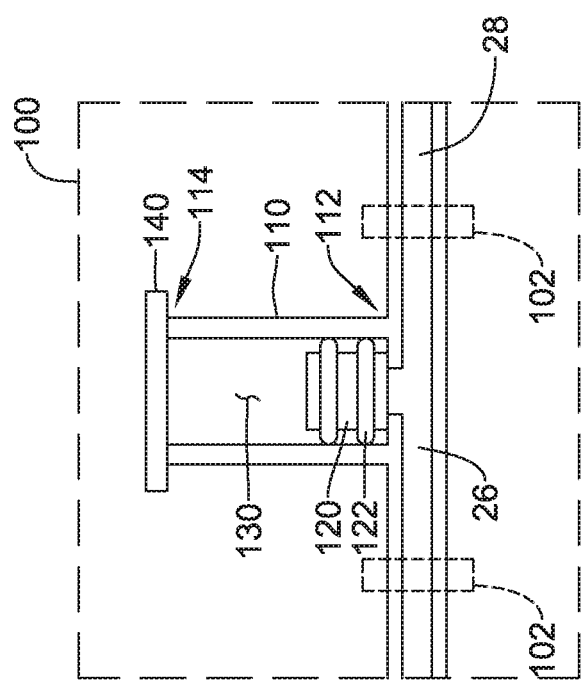

FIG. 5 illustrates a partial cross-sectional view of another example of the dampening element 100. The dampening element 100 may be positioned and/or disposed between the first segment 26 of the fluid pathway and the second segment 28 of the fluid pathway. In some instances the dampening element 100 may be provided as a disposable tubing set with tubing extending from the dampening element 100 defining the first segment 26 and/or the second segment 28, which may be removably engaged with the fluid pump 20 for moving fluid therethrough. Similar to other embodiments herein, the dampening element 100 may comprise one or more barrels 110, each barrel 110 including the movable seal member 120 disposed within the barrel 110 (and/or a lumen defined by the barrel 110), the biasing member 130 disposed within the barrel 110 (and/or the lumen defined by the barrel 110) and engaged with the movable seal member 120, and the cap 140 secured to the barrel 110 opposite the fluid pathway. The lumen of the barrel 110 may be a cylindrical lumen with the movable seal member 120 sealingly engaged with the cylindrical inner surface defining the lumen. The first end 112 of each of the one or more barrels 110 (and/or each of the lumens defined by the one or more barrels 110) may include a port in fluid communication with the fluid pathway, and the cap 140 may be secured to the opposing second end 114 of the barrel 110 (and/or the lumen defined by the barrel 110). The movable seal member 120 may be disposed within the barrel 110 (and/or the lumen defined by the barrel 110) between the port leading to the fluid pathway and the cap 140. The movable seal member 120 may be configured to sealingly engage an inner surface and/or an inner wall of the barrel 110. In some embodiments, the movable seal member 120 may include at least one sealing element 122 extending around the perimeter of the movable seal member 120 and configured to sealingly engage the inner surface and/or the inner wall of the barrel 110. For example, in some embodiments, the at least one sealing element 122 may include at least one O-ring (e.g., one O-ring, two O-rings, three O-rings, etc.) extending around the movable seal member 120 and configured to sealingly engage the inner surface and/or the inner wall of the barrel 110.

The movable seal member 120 may be configured to translate axially within the one or more barrels 110 and/or within the lumen defined by the one or more barrels 110. In some embodiments, using two or more sealing elements 122 may help to prevent tilting, cocking, and/or wedging of the movable seal member 120 within the barrel 110 and/or the lumen defined by the barrel 110. The dampening element 100 may be configured to be responsive to pressure fluctuations of the pulsatile fluid flow to actively dampen the pressure fluctuations and smoothen the pulsatile fluid flow. In the example of FIG. 5, the biasing member 130 may be a trapped gas within the barrel 110 and/or the lumen defined by the barrel 110. In some embodiments, the trapped gas may be a compressed gas (i.e., a gas at a pressure greater than 14.7 psi) or a gas at atmospheric pressure (14.7 psi), such as atmospheric air. In the example of FIG. 5, the biasing member 130 (i.e., the trapped gas) may be disposed in within the barrel 110 between the movable seal member 120 and the cap 140. In some embodiments the volume may be filled with atmospheric air during assembly and then trapped when the cap 140 is secured to the barrel 110. Accordingly, the dampening element 100 may be configured to actively dampen pressure fluctuations of the pulsatile fluid flow in the distal direction (e.g., positive flow; during infusion). The biasing member 130 may bias and/or urge the movable seal member 120 toward and/or into an initial position proximate the first end 112. The movable seal member 120, in the initial position, may be at the first end 112 of the barrel 110 immediately adjacent to the port of the barrel 110 in fluid communication with the fluid pathway and/or the first segment 26 and/or the second segment 28.

As fluid flow and/or pressure increases, fluid may flow into the barrel 110 through the port and apply a force against the movable seal member 120, thereby urging the movable seal member 120 away from the fluid pathway and/or away from the initial position at the first end 112 and toward the second end 114 of the barrel 110, and the biasing member 130 (i.e., the trapped gas) exerts a biasing force against the movable seal member 120. For example, the compressed gas may be further compressed between the movable seal member 120 and the cap 140 as the volume of trapped air decreases to apply the biasing force, or the atmospheric air may increase in pressure greater than atmospheric pressure as the volume of trapped air decreases to apply the biasing force. This permits a portion of the fluid volume to be stored within the one or more barrels 110 of the dampening element 100 to compensate for the positive volume (+dv), which results in a reduced peak pressure and/or flow rate through the fluid pathway downstream of the dampening element 100. The fluid volume that may be "stored" within the dampening element 100 may be calculated as the product of the cross-sectional area of the lumen of the barrel 110 and the axial displacement, length, or distance the movable seal member 120 is moved away from the initial position (e.g., $dv=A*L$). The relationship between the "stored" fluid volume (dv) and pressure change can be calculated using Boyle's law $(Po*Vo)=(Pf*Vf)$, wherein Po=original pressure of compressed gas, Pf=final pressure of compressed gas, Vo=original volume of compressed gas, and Vf=final volume of compressed gas. The volume of stored fluid can be calculated using the equation: $dv=Vo*(Pf-Po)/Pf$.

In at least some embodiments wherein the biasing member 130 includes a trapped gas, the cap 140 may include a seal member rendering the portion of the barrel 110 and/or the lumen defined by the barrel 110 further defined by the side of the movable seal member 120 opposite the fluid pathway and/or the at least one sealing element 122 axially farthest away from the fluid pathway fluidtight, thereby permitting compression of the trapped gas therein as the fluid volume is stored in the dampening element 100. The biasing force of the compressed gas trapped within the barrel 110 may be increased by axial translation of the movable seal member 120 toward the second end 114, which reduces the volume of the trapped gas.

Figure 6:
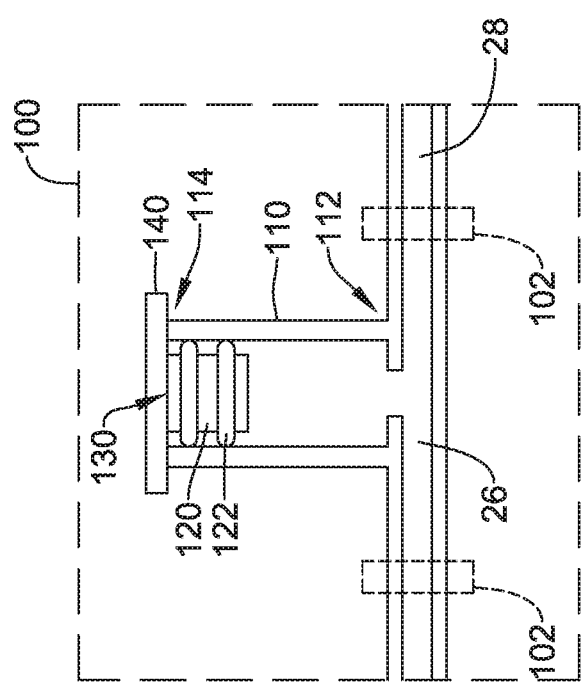

FIG. 6 illustrates a partial cross-sectional view of another example of the dampening element 100. The dampening element 100 may be positioned and/or disposed between the first segment 26 of the fluid pathway and the second segment 28 of the fluid pathway. In some instances the dampening element 100 may be provided as a disposable tubing set with tubing extending from the dampening element 100 defining the first segment 26 and/or the second segment 28, which may be removably engaged with the fluid pump 20 for moving fluid therethrough. Similar to other embodiments herein, the dampening element 100 may comprise one or more barrels 110, each barrel 110 including the movable seal member 120 disposed within the barrel 110 (and/or the lumen defined by the barrel 110), the biasing member 130 disposed within the barrel 110 (and/or the lumen defined by the barrel 110) and engaged with the movable seal member 120, and the cap 140 secured to the barrel 110 opposite the fluid pathway. The first end 112 of each of the one or more barrels 110 (and/or each of the lumens defined by the one or more barrels 110) may include a port in fluid communication with the fluid pathway, and the cap 140 may be secured to the opposing second end 114 of the barrel 110 (and/or the lumen defined by the barrel 110). The movable seal member 120 may be disposed within the barrel 110 (and/or the lumen defined by the barrel 110) between the port leading to the fluid pathway and the cap 140. The movable seal member 120 may be configured to sealingly engage the inner surface and/or the inner wall of the barrel 110. The lumen of the barrel 110 may be a cylindrical lumen with the movable seal member 120 sealingly engaged with the cylindrical inner surface defining the lumen. In some embodiments, the movable seal member 120 may include at least one sealing element 122 extending around the perimeter of the movable seal member 120 and configured to sealingly engage the inner surface and/or the inner wall of the barrel 110. For example, in some embodiments, the at least one sealing element 122 may include at least one O-ring (e.g., one O-ring, two O-rings, three O-rings, etc.) extending around the movable seal member 120 and configured to sealingly engage the inner surface and/or the inner wall of the barrel 110.

The movable seal member 120 may be configured to translate axially within the one or more barrels 110 and/or within the lumen defined by the one or more barrels 110. In some embodiments, using two or more sealing elements 122 may help to prevent tilting, cocking, and/or wedging of the movable seal member 120 within the barrel 110 and/or the lumen defined by the barrel 110. The dampening element 100 may be configured to be responsive to pressure fluctuations of the pulsatile fluid flow to actively dampen the pressure fluctuations and smoothen the pulsatile fluid flow. In the example of FIG. 6, the biasing member 130 may be a gas at atmospheric pressure (14.7 psi), such as atmospheric air, or a vacuum or a partial vacuum trapped within the barrel 110 and/or the lumen defined by the barrel 110. In the example of FIG. 6, the biasing member 130 may be disposed within the barrel 110 between the movable seal member 120 and the cap 140. In some embodiments the volume may be filled with atmospheric air during assembly and then trapped when the cap 140 is secured to the barrel 110. Accordingly, the dampening element 100 may be configured to actively dampen pressure fluctuations of the pulsatile fluid flow in the proximal direction (e.g., negative flow; during suction). The biasing member 130 may bias and/or urge the movable seal member 120 toward and/or into an initial position proximate the second end 114 or otherwise position the movable seal member 120 toward the second end 114. The movable seal member 120, in the initial position, may be at the second end 114 of the barrel 110 immediately adjacent to and/or in contact with the cap 140.

During pulsatile fluid flow in the distal direction (e.g., positive flow; during infusion) and/or during periods of low flow and low suction in the proximal direction (e.g., negative flow; during suction), fluid may flow into the barrel 110 and/or the lumen defined by the barrel 110 between the first end 112 and the movable seal member 120. The volume of gas forming the biasing element 130 generates a biasing force (i.e. vacuum or partial vacuum) as the movable seal member 120 is pulled toward the port leading to the fluid pathway. As the suction or negative pressure increases in magnitude to a point where the suctioning force exceeds the biasing force of the biasing member 130, fluid may be drawn out of the barrel 110, thereby "pulling" the movable seal member 120 away from the cap 140 and/or away from the initial position at the second end 114 and toward the first end 112 of the barrel 110. This permits a portion of the fluid volume to be released from the one or more barrels 110 of the dampening element 100 to compensate for the negative volume (−dv), which results in a smoothened pressure and/or flow rate through the fluid pathway.

In at least some embodiments wherein the biasing member 130 includes a gas at atmospheric pressure or the vacuum or the partial vacuum, the cap 140 may include a seal member rendering the portion of the barrel 110 and/or the lumen defined by the barrel 110 further defined by the side of the movable seal member 120 opposite the fluid pathway and/or the at least one sealing element 122 axially farthest away from the fluid pathway fluidtight, and the biasing force of the vacuum or partial vacuum trapped within the barrel 110 may be increased by axial translation of the movable seal member 120 toward the first end 112.

Figure 7:
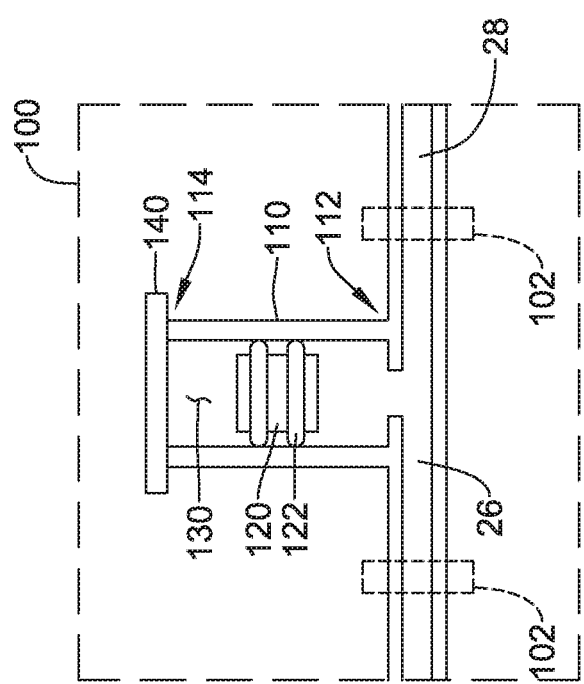

FIG. 7 illustrates a partial cross-sectional view of one example of the dampening element 100 that effectively combines the examples of FIGS. 5 and 6. The dampening element 100 may be positioned and/or disposed between the first segment 26 of the fluid pathway and the second segment 28 of the fluid pathway such that the dampening element 100 is in fluid communication with the fluid pathway. Similar to other embodiments described herein, the dampening element 100 may comprise one or more barrels 110, each barrel 110 including the movable seal member 120 disposed within the barrel 110 (and/or a lumen defined by the barrel 110), the biasing member 130 disposed within the barrel 110 (and/or the lumen defined by the barrel 110) and engaged with the movable seal member 120, and the cap 140 secured to the barrel 110 opposite the fluid pathway. The first end 112 of each of the one or more barrels 110 (and/or each of the lumens defined by the one or more barrels 110) may include a port in fluid communication with the fluid pathway, and the cap 140 may be secured to the opposing second end 114 of the barrel 110 (and/or the lumen defined by the barrel 110). The movable seal member 120 may be disposed within the barrel 110 (and/or the lumen defined by the barrel 110) between the fluid pathway and the cap 140. The movable seal member 120 may be configured to sealingly engage an inner surface and/or an inner wall of the barrel 110. The lumen of the barrel 110 may be a cylindrical lumen with the movable seal member 120 sealingly engaged with the cylindrical inner surface defining the lumen. In some embodiments, the movable seal member 120 may include at least one sealing element 122 extending around the perimeter of the movable seal member 120 and configured to sealingly engage the inner surface and/or the inner wall of the barrel 110. For example, in some embodiments, the at least one sealing element 122 may include at least one O-ring (e.g., one O-ring, two O-rings, three O-rings, etc.) extending around the movable seal member 120 and configured to sealingly engage the inner surface and/or the inner wall of the barrel 110.

The movable seal member 120 may be configured to translate axially within the one or more barrels 110 and/or within the lumen defined by the one or more barrels 110. In some embodiments, using two or more sealing elements 122 may help to prevent tilting, cocking, and/or wedging of the movable seal member 120 within the barrel 110 and/or the lumen defined by the barrel 110. The dampening element 100 may be configured to be responsive to pressure fluctuations of the pulsatile fluid flow to actively dampen the pressure fluctuations and smoothen the pulsatile fluid flow. In the example of FIG. 7, the biasing member 130 may be a trapped gas occupying a volume of space within the barrel 110 and/or the lumen defined by the barrel 110 at equilibrium, such as at atmospheric pressure (14. 7 psi). In some embodiments the volume may be filled with atmospheric air during assembly and then trapped when the cap 140 is secured to the barrel 110. In the example of FIG. 7, the volume of trapped gas forming the biasing member 130 may be disposed in within the barrel 110 between the movable seal member 120 and the cap 140. Accordingly, the dampening element 100 may be configured to actively dampen pressure fluctuations of the pulsatile fluid flow in the distal direction (e.g., positive flow; during infusion), in the proximal direction (e.g., negative flow; during suction), and/or in both flow directions during operation of the pump. The movable seal member 120 may translate axially within the barrel 110 in either direction, depending on whether the system is experiencing positive pressure and/or flow spikes or negative pressure and/or flow spikes. As the movable seal member 120 translates axially within the barrel 110, the characteristics of the biasing member 130 and/or the trapped gas within the barrel 110 may be altered, resulting in compression of the trapped gas (as a consequence of decreasing the volume of trapped gas) or generating a vacuum or partial vacuum as a consequence of increasing the volume of trapped gas. For example, as the movable seal member 120 is displaced or translates axially toward the second end 114, the trapped gas is compressed, thereby generating a biasing force urging the movable seal member 120 towards the first end 112 and/or the initial position, and as the movable seal member 120 is displaced or translates axially toward the first end 112, the trapped gas is expanded and/or subjected to a vacuum or partial vacuum, thereby generating a biasing force urging the movable seal member 120 towards the second end 114 and/or the initial position.

As the fluid flow and/or pressure increases, fluid may flow into the barrel 110 through the port and apply a force against the movable seal member 120, thereby urging the movable seal member 120 away from the fluid pathway and/or away from the initial, equilibrium position (intermediate the first end 112 and the second end 114) and toward the second end 114 of the barrel 110, and the biasing member 130 (i.e., the gas) may be compressed between the movable seal member 120 and the cap 140 exerting a biasing force against the movable seal member 120. This permits a portion of the fluid volume to be stored within the one or more barrels 110 of the dampening element 100 to compensate for the positive volume (+dv), which results in a reduced peak pressure and/or flow rate through the fluid pathway downstream of the dampening element 100. The fluid volume that may be "stored" within the dampening element 100 may be calculated as the product of the cross-sectional area of the lumen of the barrel 110 and the axial displacement, length, or distance the movable seal member 120 is moved away from the initial position (e.g., dv=A*L). The relationship between the "stored" fluid volume (dv) and pressure change can be calculated using Boyle's law (Po*Vo)=(Pf*Vf), wherein Po=original pressure of compressed gas, Pf=final pressure of compressed gas, Vo=original volume of compressed gas, and Vf=final volume of compressed gas. The volume of stored fluid can be calculated using the equation: dv=Vo*(Pf−Po)/Pf.

As the suction and/or the negative pressure increases in magnitude with fluid flow in the proximal direction, fluid may be suctioned out of the barrel 110, thereby "pulling" the movable seal member 120 away from the cap 140 and/or away from the initial position and toward the first end 112 of the barrel 110. This permits a portion of the fluid volume to be released from the one or more barrels 110 of the dampening element 100 to compensate for the negative volume (−dv), which results in an increased minimum pressure and/or flow rate through the fluid pathway. The biasing force of the vacuum or partial vacuum trapped within the barrel 110 may be increased by axial translation of the movable seal member 120 toward the first end 112.

Figure 8:
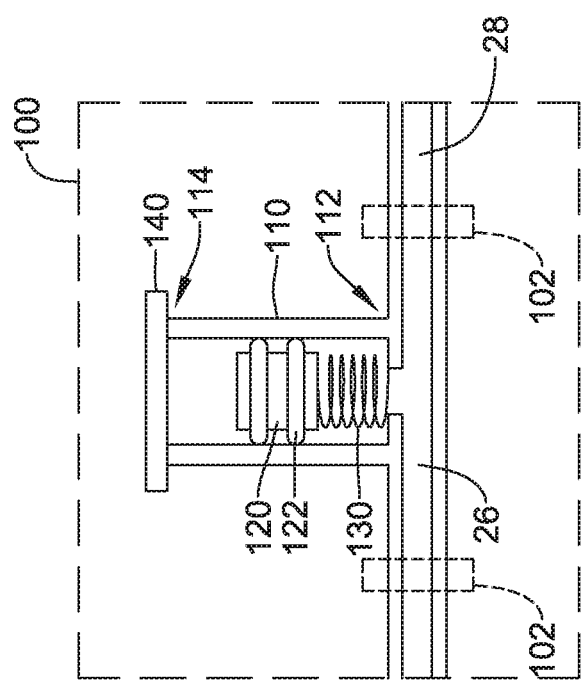

FIG. 8 illustrates a partial cross-sectional view of one example of the dampening element 100. The dampening element 100 may be positioned and/or disposed between the first segment 26 of the fluid pathway and the second segment 28 of the fluid pathway such that the dampening element 100 is in fluid communication with the fluid pathway. Similar to other embodiments described herein, the dampening element 100 may comprise one or more barrels 110, each barrel 110 including a movable seal member 120 disposed within the barrel 110 (and/or a lumen defined by the barrel 110), a biasing member 130 disposed within the barrel 110 (and/or the lumen defined by the barrel 110) and engaged with the movable seal member 120, and a cap 140 secured to the barrel 110 opposite the fluid pathway. The first end 112 of each of the one or more barrels 110 (and/or each of the lumens defined by the one or more barrels 110) may include a port in fluid communication with the fluid pathway, and the cap 140 may be secured to an opposing second end 114 of the barrel 110 (and/or the lumen defined by the barrel 110). The movable seal member 120 may be disposed within the barrel 110 (and/or the lumen defined by the barrel 110) between the fluid pathway and the cap 140. The movable seal member 120 may be configured to sealingly engage an inner surface and/or an inner wall of the barrel 110. The lumen of the barrel 110 may be a cylindrical lumen with the movable seal member 120 sealingly engaged with the cylindrical inner surface defining the lumen. In some embodiments, the movable seal member 120 may include at least one sealing element 122 extending around a perimeter of the movable seal member 120 and configured to sealingly engage the inner surface and/or the inner wall of the barrel 110. For example, in some embodiments, the at least one sealing element 122 may include at least one O-ring (e.g., one O-ring, two O-rings, three O-rings, etc.) extending around the movable seal member 120 and configured to sealingly engage the inner surface and/or the inner wall of the barrel 110.

The movable seal member 120 may be configured to translate axially within the one or more barrels 110 and/or within the lumen defined by the one or more barrels 110. In some embodiments, using two or more sealing elements 122 may help to prevent tilting, cocking, and/or wedging of the movable seal member 120 within the barrel 110 and/or the lumen defined by the barrel 110. The dampening element 100 may be configured to be responsive to pressure fluctuations of the pulsatile fluid flow to actively dampen the pressure fluctuations and smoothen the pulsatile fluid flow. In the example of FIG. 8, the biasing member 130 may be an elastic element that is axially compressible and axially extendable. In some embodiments, the elastic element may be a spring, an expandable/compressible member, or other similar structure or element. In the example of FIG. 8, the spring may be secured in equilibrium within the barrel 110 between the movable seal member 120 and the first end 112 of the barrel 110. Additionally, in some embodiments, the dampening element 100 may include a second biasing member. The second biasing member may be a trapped gas disposed between the movable seal member 120 and the cap 140 at equilibrium. In some embodiments, the second biasing member may be compressed gas acting against the spring. Accordingly, the dampening element 100 may be configured to actively dampen pressure fluctuations of the pulsatile fluid flow in the proximal direction (e.g., negative flow; during suction) and the distal direction (e.g., positive flow; during infusion). The biasing member 130 and/or the second biasing member may position the movable seal member 120 at an initial, equilibrium position intermediate the first end 112 and the second end 114 of the barrel 110. In some embodiments, when the movable seal member 120 is at the initial position, the biasing member 130 may be in equilibrium, but able to axially compress and axially elongate when subjected to a force acting on the movable seal member 120 that moves the movable seal member 120 within the barrel 110. As the movable seal member 120 translates axially toward the second end 114, the spring may be stretched in tension, generating a biasing force biasing the movable seal member 120 towards the initial position. As the movable seal member 120 translates axially toward the first end 112, the spring may be compressed in compression generating a biasing force biasing the movable seal member 120 towards the initial position.

As the fluid flow and/or pressure increases, fluid may flow into the barrel 110 through the port and apply a force against the movable seal member 120, thereby urging the movable seal member 120 away from the fluid pathway and/or away from the initial, equilibrium position (intermediate the first end 112 and the second end 114) and toward the second end 114 of the barrel 110. This permits a portion of the fluid volume to be stored within the one or more barrels 110 of the dampening element 100 to compensate for the positive volume (+dv), which results in a reduced peak pressure and/or flow rate through the fluid pathway downstream of the dampening element 100. The fluid volume that may be "stored" within the dampening element 100 may be calculated as the product of the cross-sectional area of the lumen of the barrel 110 and the axial displacement, length, or distance the movable seal member 120 is moved away from the initial position (e.g., dv=A*L). The biasing force exerted by the elastic element (e.g., the biasing member 130) may be calculated using Hooke's law (e.g., F=−kx; where k is the rate or spring constant and x is the displacement length of the elastic element from its equilibrium position). As the suction and/or the negative pressure increases in magnitude with fluid flow in the proximal direction, fluid may be suctioned out of the barrel 110, thereby "pulling" the movable seal member 120 away from the initial position and toward the first end 112 of the barrel 110. This permits a portion of the fluid volume to be released from the one or more barrels 110 of the dampening element 100 to compensate for the negative volume (−dv), which results in an increased minimum pressure and/or flow rate through the fluid pathway.

Figure 9:
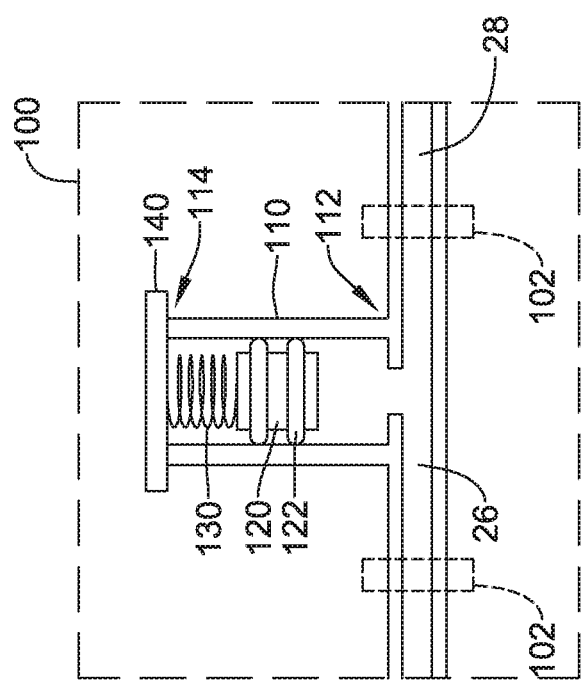

FIG. 9 illustrates a partial cross-sectional view of another example of the dampening element 100 similar to the embodiment of FIG. 8, except the biasing member 130 (e.g., spring) is arranged between the movable seal member 120 and the cap 140 of the barrel 110. In the example of FIG. 9, the spring may be secured in equilibrium within the barrel 110 between the movable seal member 120 and the second end 114 of the barrel 110. Accordingly, the dampening element 100 may be configured to actively dampen pressure fluctuations of the pulsatile fluid flow in the proximal direction (e.g., negative flow; during suction) and the distal direction (e.g., positive flow; during infusion). The biasing member 130 may position the movable seal member 120 at an initial, equilibrium position intermediate the first end 112 and the second end 114 of the barrel 110. In some embodiments, when the movable seal member 120 is at the initial position, the biasing member 130 may be in equilibrium, but able to axially compress and axially elongate when subjected to a force acting on the movable seal member 120 that moves the movable seal member 120 within the barrel 110. As the movable seal member 120 translates axially toward the first end 112, the spring may be stretched in tension, generating a biasing force biasing the movable seal member 120 towards the initial position. As the movable seal member 120 translates axially toward the second end 114, the spring may be compressed in compression generating a biasing force biasing the movable seal member 120 towards the initial position.

As the fluid flow and/or pressure increases, fluid may flow into the barrel 110 through the port and apply a force against the movable seal member 120, thereby urging the movable seal member 120 away from the fluid pathway and/or away from the initial, equilibrium position (intermediate the first end 112 and the second end 114) and toward the second end 114 of the barrel 110. This permits a portion of the fluid volume to be stored within the one or more barrels 110 of the dampening element 100 to compensate for the positive volume (+dv), which results in a reduced peak pressure and/or flow rate through the fluid pathway downstream of the dampening element 100. The fluid volume that may be "stored" within the dampening element 100 may be calculated as the product of the cross-sectional area of the lumen of the barrel 110 and the axial displacement, length, or distance the movable seal member 120 is moved away from the initial position (e.g., dv=A*L). The biasing force exerted by the elastic element (e.g., the biasing member 130) may be calculated using Hooke's law (e.g., F=−kx; where k is the rate or spring constant and x is the displacement length of the elastic element from its equilibrium position).

As the suction and/or the negative pressure increases in magnitude with fluid flow in the proximal direction, fluid may be suctioned out of the barrel 110, thereby "pulling" the movable seal member 120 away from the initial position and toward the first end 112 of the barrel 110. This permits a portion of the fluid volume to be released from the one or more barrels 110 of the dampening element 100 to compensate for the negative volume (−dv), which results in an increased minimum pressure and/or flow rate through the fluid pathway.

Figure 10:
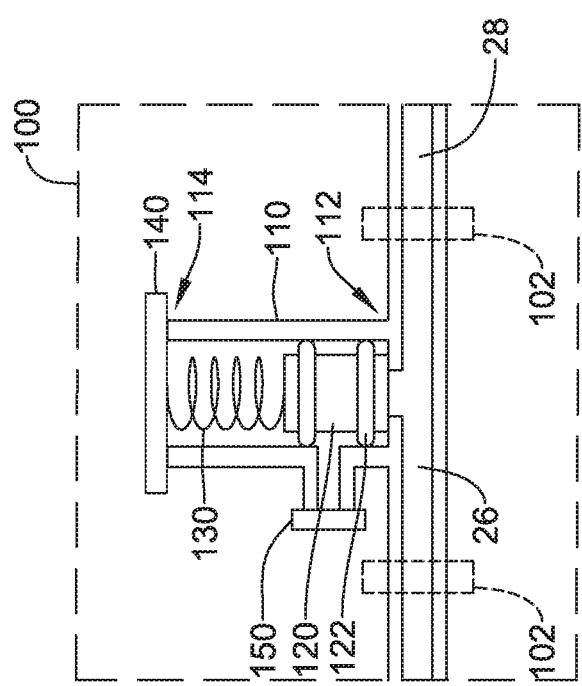
FIG. 10 illustrates an example pressure relief port associated with an example dampening element.

FIG. 10 illustrates a partial cross-sectional view of another example of the dampening element 100. The example illustrated in FIG. 10 is substantially the same as that illustrated in FIG. 3, with an additional feature added. However, it will be appreciated that the additional feature of FIG. 10 may work equally well in any and/or all embodiments and/or examples of the dampening element 100 disclosed herein—including, but not limited to, the examples of FIGS. 4-9. Likewise, the additional feature of FIG. 10 may be included in any and/or all of the examples that follow FIG. 10. The dampening element 100 illustrated in FIG. 10 further includes a pressure relief port 150 in fluid communication with the barrel 110 and/or the lumen defined by the barrel 110. As may be appreciated, the pressure relief port 150 may be opened or closed when the fluid pressure within the barrel 110 and/or the lumen defined by the barrel 110 exceeds a pressure threshold.

In the example of FIG. 10, the biasing member 130 may be positioned within the barrel 110 between the movable seal member 120 and the cap 140. Accordingly, the dampening element 100 may be configured to actively dampen pressure fluctuations of the pulsatile fluid flow in the distal direction (e.g., positive flow; during infusion). The biasing member 130 may bias and/or urge the movable seal member 120 toward and/or into the initial position proximate the first end 112. In the initial position, and/or during any axial translation of the movable seal member 120, the at least one sealing element 122 disposed closest to the second end 114 of the barrel 110 may form a fluidtight seal between the pressure relief port 150 and the cap 140 (and/or the second end 114 of the barrel 110). For example, the pressure relief port 150 and/or the fluid pathway may be fluidly and completely sealed off from the second end 114 of the barrel 110 and/or the cap 140. In some embodiments, the at least one sealing element 122 disposed closest to the second end 114 of the barrel 110 may always be disposed between the pressure relief port 150 and the second end 114 of the barrel 110 and/or the cap 140, and the at least one sealing element 122 disposed closest to the first end 112 of the barrel 110 may be disposed between the pressure relief port 150 and the first end 112 of the barrel 110, except when a fluid pressure exceeding the pressure threshold causes axial translation of the movable seal member 120 toward the second end 114 of the barrel 110 a sufficient distance to place the fluid in the fluid pathway in fluid communication with the pressure relief port 150.

As the fluid flow and/or pressure increases, fluid may flow into the barrel 110 from the fluid pathway and apply a force against the movable seal member 120, thereby urging the movable seal member 120 away from the fluid pathway and/or away from the initial, equilibrium position at the first end 112 and toward the second end 114 of the barrel 110, and the biasing member 130 may be compressed. This permits a portion of the fluid volume to be stored within the one or more barrels 110 of the dampening element 100 to compensate for the positive volume (+dv), which results in a reduced peak pressure and/or flow rate through the fluid pathway downstream of the dampening element 100. Additionally, as the movable seal member 120 translates toward the cap 140 and/or the second end 114 of the barrel 110, the end of the movable seal member 120 (and/or the at least one sealing element 122) closest to the first end 112 may translate axially past the pressure relief port 150 when the fluid exceeds a threshold pressure level, thereby placing the fluid in fluid communication with the pressure relief port 150. The pressure relief port 150 may include a pressure relief valve that may open at a threshold pressure (which may be less than, equal to, or greater than the threshold pressure necessary to move the movable seal member 120 sufficiently to place the fluid in fluid communication with the pressure relief port 150) and permitting a portion of the fluid flowing into the barrel 110 to flow out of the pressure relief port 150. As the fluid pressure and/or flow is reduced below the threshold, the movable seal member 120 translates toward the first end 112 of the barrel 110, and the end of the movable seal member 120 (and/or the at least one sealing element 122) closest to the first end 112 may translate axially past the pressure relief port 150, thereby closing the pressure relief port 150 and isolating the fluid in the fluid pathway from the pressure relief port 150.

Figure 11:
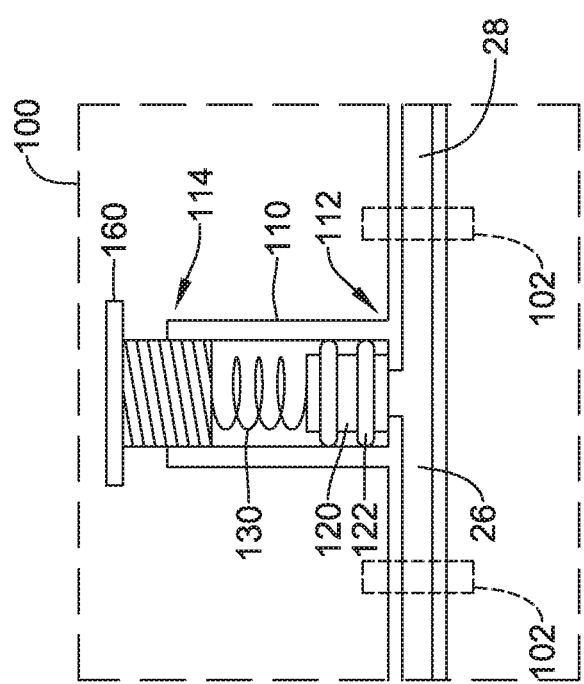
FIGS. 11-14 illustrates an example adjustable cap associated with an example dampening element.

FIG. 11 illustrates a partial cross-sectional view of another example of the dampening element 100. The example illustrated in FIG. 11 is substantially the same as that illustrated in FIG. 3, with an additional feature added. However, it will be appreciated that the additional feature of FIG. 11 may work equally well in any and/or all embodiments and/or examples of the dampening element 100 disclosed herein—including, but not limited to, the examples of FIGS. 4-10. Likewise, the additional feature of FIG. 11 may be included in any and/or all of the examples that follow FIG. 11. The dampening element 100 illustrated in FIG. 11 further includes an adjustment mechanism, such as an adjustable cap 160 for adjusting the biasing force and/or amount of translation of the movable seal member 130 permitted. In some embodiments, each of the one or more barrels 110 may include an adjustable cap 160. In some configurations, one or more barrels 110 may include an adjustable cap 160, and one or more barrels 110 may include the non-adjustable cap 140 (not shown in FIG. 11), in varying combination(s). As may be appreciated, the adjustable cap 160 may be configured to adjust a working length of the barrel 110 and/or the biasing force of the biasing member 130. In at least some embodiments, some and/or each adjustable cap 160 may be configured to threadably engage its respective barrel 110, wherein rotation of the adjustable cap 160 relative to the barrel 110 translates the adjustable cap 160 axially to adjust the working length of the barrel 110 and/or the biasing force of the biasing member 130. Alternatively, in some embodiments, the adjustable cap 160 may be configured to engage its respective barrel 110 using a camming mechanism, or other suitable engagement means. As may be appreciated, translating the adjustable cap 160 towards the first end 112 of the barrel 110 may further compress the biasing member 130, may increase the bias toward the first end of the barrel 110, and/or may increase the bias force applied to the movable seal member 120 by the biasing member 130 at an initial position. Similarly, translating the adjustable cap 160 away from the first end 112 of the barrel 110 and/or towards the second end 114 of the barrel 110 may decompress the biasing member 130, may decrease the bias toward the first end of the barrel 110, and/or may decrease the bias force applied to the movable seal member 120 by the biasing member 130 at an initial position. Thus, a user may adjust the adjustment cap 160, or other adjustment mechanism, to provide a desired responsiveness of the dampening element 100 to pressure and/or flow fluctuations during a medical procedure.

Figure 12:
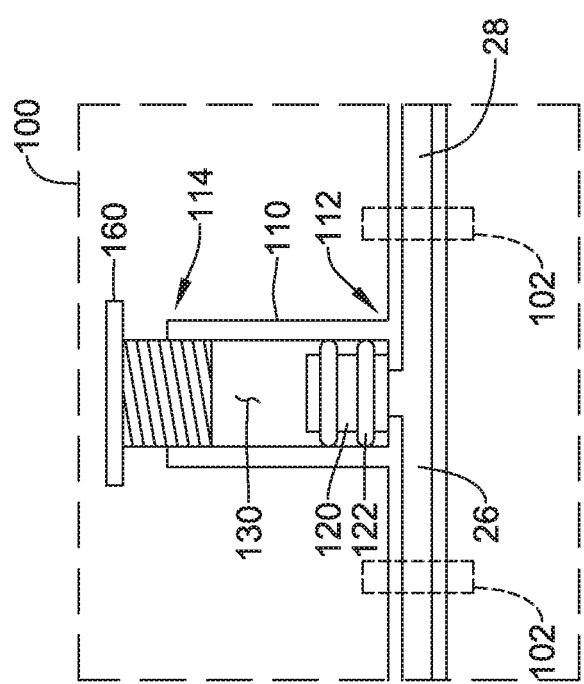

FIG. 12 illustrates a partial cross-sectional view of another example of the dampening element 100. The example illustrated in FIG. 12 is substantially the same as that illustrated in FIG. 5, with an additional feature added. However, it will be appreciated that the additional feature of FIG. 12 may work equally well in any and/or all embodiments and/or examples of the dampening element 100 disclosed herein—including, but not limited to, the examples of FIGS. 5-7. Likewise, the additional feature of FIG. 12 may be included in any and/or all of the examples that follow FIG. 12. The dampening element 100 illustrated in FIG. 12 further includes an adjustment mechanism, such as an adjustable cap 160 for adjusting the biasing force and/or amount of translation of the movable seal member 130 permitted. In some embodiments, each of the one or more barrels 110 may include an adjustable cap 160. In some configurations, one or more barrels 110 may include an adjustable cap 160, and one or more barrels 110 may include the non-adjustable cap 140 (not shown in FIG. 12), in varying combination(s). As may be appreciated, the adjustable cap 160 may be configured to adjust a working length of the barrel 110 and thus the volume of the trapped gas in the initial position. In at least some embodiments, some and/or each adjustable cap 160 may be configured to threadably engage its respective barrel 110, wherein rotation of the adjustable cap 160 relative to the barrel 110 translates the adjustable cap 160 axially to adjust the working length of the barrel 110 and thus the volume of the trapped gas in the initial position. Alternatively, in some embodiments, the adjustable cap 160 may be configured to engage its respective barrel 110 using a camming mechanism, or other suitable engagement means. As may be appreciated, translating the adjustable cap 160 towards the first end 112 of the barrel 110 may further compress the biasing member 130 (e.g., the trapped gas), may increase the bias toward the first end of the barrel 110, and/or may increase the bias force applied to the movable seal member 120 by the biasing member 130. For example, translating the adjustable cap 160 towards the first end 112 of the barrel 110 may reduce the volume and thus compress and increase the pressure of the trapped gas within the barrel 110. Similarly, translating the adjustable cap 160 away from the first end 112 of the barrel 110 and/or towards the second end 114 of the barrel 110 may increase the volume and thus decompress the biasing member 130 (e.g., the trapped gas), may decrease the bias toward the first end of the barrel 110, and/or may decrease the bias force applied to the movable seal member 120 by the biasing member 130. For example, translating the adjustable cap 160 towards the second end 114 of the barrel 110 may decompress and decrease the pressure of the trapped gas within the barrel 110. Alternatively and/or additionally, the adjustable cap 160 may be used in embodiments and/or examples where the biasing member 130 is a vacuum or partial vacuum disposed and/or trapped within the barrel 110.

Figure 13:
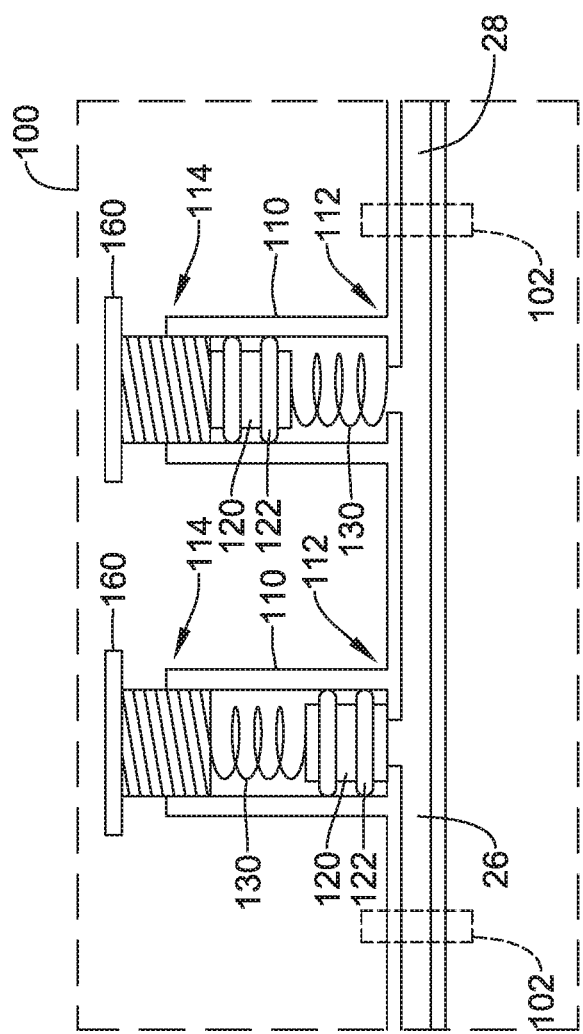

FIG. 13 illustrates a partial cross-sectional view of another example of the dampening element 100. The example illustrated in FIG. 13 combines selected features of the examples illustrated in FIGS. 3 and 4. However, it will be appreciated that the example of FIG. 13 may work equally well in and/or with features from any and/or all embodiments and/or examples of the dampening element 100 disclosed herein. Similarly, additional arrangements and/or combinations of features are also contemplated.

The dampening element 100 may be positioned and/or disposed between the first segment 26 of the fluid pathway and the second segment 28 of the fluid pathway. The dampening element 100 may be in fluid communication with the fluid pathway, and in some instances the dampening element 100 may be provided as a disposable tubing set with tubing extending from the dampening element 100 defining the first segment 26 and/or the second segment 28, which may be removably engaged with the fluid pump 20 for moving fluid therethrough. The dampening element 100 may comprise a plurality of barrels 110, each barrel 110 including a movable seal member 120 disposed within the barrel 110 (and/or a lumen defined by the barrel 110), a biasing member 130 disposed within the barrel 110 (and/or the lumen defined by the barrel 110) and engaged with the movable seal member 120, and a cap 140 (not shown in FIG. 13) secured to the barrel 110 opposite the fluid pathway. The cap 140 may be selectively lockable onto the barrel 110. Alternatively, some of and/or each barrel 110 may comprise an adjustable cap 160 as described herein.

In the example illustrated in FIG. 13, the plurality of barrels 110 may include and/or comprise a first barrel 110 and a second barrel 110. In at least some embodiments, the first barrel 110 and the second barrel 110 are both positioned between the fluid pump 20 and the fluid flow sensor 190 and/or the medical device 30. Other arrangements and/or configurations, including but not limited to three barrels, four barrels, five barrels, or more barrels, are also contemplated. The first barrel 110 may include a first movable seal member 120 disposed within the first barrel 110 (and/or the lumen defined by the first barrel 110) and a first biasing member 130 disposed within the first barrel 110 (and/or the lumen defined by the first barrel 110) and engaged with the first movable seal member 120. The second barrel 110 may include a second movable seal member 120 disposed within the second barrel 110 (and/or the lumen defined by the second barrel 110) and a second biasing member 130 disposed within the second barrel 110 (and/or the lumen defined by the second barrel 110) and engaged with the second movable seal member 120. In some embodiments, the first barrel 110 and the second barrel 110 may be formed as a unified housing. In some embodiments, the first barrel 110 may be structurally and/or functionally independent of the second barrel 110. As such, multiple first barrels and/or multiple second barrels may be utilized and/or included within the dampening element 100. In some embodiments, the fluid volume(s) desired to be accommodated by the one or more barrels 110 may be divided into several barrels placed in series with each other, thereby providing an additive configuration capable of accommodating a greater volume of fluid and/or a higher pressure pulse.

In should be noted that the orientation and positioning of the first barrel 110 and the second barrel 110 relative to each other and/or relative to the fluid pathway may be varied while maintaining the desired function(s) and/or benefits of the dampening element 100. In the view illustrated, the first barrel 110 and the second barrel 110 both extend upward from the fluid pathway and/or the first segment 26 and the second segment 28. In some embodiments, one of the first barrel 110 or the second barrel 110 may extend upward from the fluid pathway and/or the first segment 26 and the second segment 28 and the other of the first barrel 110 or the second barrel 110 may extend downward from the fluid pathway and/or the first segment 26 and the second segment 28. Alternatively, one of the first barrel 110 or the second barrel 110 may extend at a non-zero angle (e.g., 30 degrees, 45 degrees, 60 degrees, 90 degrees, 120 degrees, 150 degrees, etc.) relative to the other of the first barrel 110 or the second barrel 110. Other arrangements and/or configurations are also contemplated. For example, in some embodiments, positioning of the first barrel 110 and the second barrel 110 may be interchanged while retaining their respective functions. In some embodiments, the dampening element 100, the first barrel 110, and/or the second barrel 110 may be positioned in any orientation relative to the fluid pathway and/or the first segment 26 and the second segment 28 while retaining its respective function(s). For example, the dampening element 100, the first barrel 110, and/or the second barrel 110 may be positioned on its side, upside down, etc. This arrangement is equally applicable to all other embodiments described and contemplated within the context of this application.

The example illustrated in FIG. 13 includes adjustable caps 160, but this is not intended to be limiting, and the cap 140 and/or the adjustable cap 160 may be used in varying combinations as described herein. Additionally, as mentioned above, in some embodiments, the dampening element 100 may include the first connector 102 and/or the second connector 102 and/or multiples thereof.

In some embodiments, a first end 112 of each of the one or more barrels 110 (and/or each of the lumens defined by the one or more barrels 110) may include a port in fluid communication with the fluid pathway, and the cap 140 and/or the adjustable cap 160 may be secured to an opposing second end 114 of the barrel 110 (and/or the lumen defined by the barrel 110). The movable seal member 120 may be disposed within the barrel 110 (and/or the lumen defined by the barrel 110) between the port leading to the fluid pathway and the cap 140 and/or the adjustable cap 160. The movable seal member 120 may be configured to sealingly engage an inner surface and/or an inner wall of the barrel 110. In some embodiments, the movable seal member 120 may include at least one sealing element 122 extending around a perimeter of the movable seal member 120 and configured to sealingly engage the inner surface and/or the inner wall of the barrel 110. For example, in some embodiments, the at least one sealing element 122 may include at least one O-ring (e.g., one O-ring, two O-rings, three O-rings, etc.) extending around the movable seal member 120 and configured to sealingly engage the inner surface and/or the inner wall of the barrel 110.

The movable seal member 120 may be configured to translate axially within the one or more barrels 110 and/or within the lumen defined by the one or more barrels 110. In some embodiments, using two or more sealing elements 122 may help to prevent tilting, cocking, and/or wedging of the movable seal member 120 within the barrel 110 and/or the lumen defined by the barrel 110. The dampening element 100 may be configured to be responsive to pressure fluctuations of the pulsatile fluid flow to actively dampen the pressure fluctuations and smoothen the pulsatile fluid flow.

In the example of FIG. 13, the first biasing member 130 (e.g., spring) may be secured in compression or equilibrium within the first barrel 110 between the first movable seal member 120 and the cap 140 and/or the adjustable cap 160. Accordingly, the dampening element 100 and/or the first barrel 110 may be configured to actively dampen pressure fluctuations of the pulsatile fluid flow in the distal direction (e.g., positive flow; during infusion). The first biasing member 130 may bias and/or urge the first movable seal member 120 toward and/or into an initial position proximate the first end 112 or otherwise position the movable seal member 120 toward the first end 112. The first movable seal member 120, in the initial position, may be at the first end 112 of the first barrel 110 immediately adjacent to the port of the first barrel 110 in fluid communication with the fluid pathway and/or the first segment 26 and/or the second segment 28. The first dampening element 100 may function similar to the dampening element 100 of FIG. 3 to be responsive to pressure fluctuations of the pulsatile fluid flow in a distal direction (e.g., positive pressure) to actively dampen the pressure fluctuations and smoothen the pulsatile fluid flow.

Furthermore, the second biasing member 130 (e.g., spring) may be secured in compression or equilibrium within the second barrel 110 between the second movable seal member 120 and the first end 112 of the second barrel 110. Accordingly, the dampening element 100 and/or the second barrel 110 may be configured to actively dampen pressure fluctuations of the pulsatile fluid flow in the proximal direction (e.g., negative flow; during suction). The second biasing member 130 may bias and/or urge the second movable seal member 120 toward and/or into an initial position proximate the second end 114 or otherwise position the movable seal member 120 toward the second end 114. The second movable seal member 120, in the initial position, may be at the second end 114 of the second barrel 110 immediately adjacent to and/or in contact with the cap 140 and/or the adjustable cap 160. The second dampening element 100 may function similar to the dampening element 100 of FIG. 4 to be responsive to pressure fluctuations of the pulsatile fluid flow in a proximal direction (e.g., negative pressure) to actively dampen the pressure fluctuations and smoothen the pulsatile fluid flow.

In addition or alternatively, the dampening element 100 may be constructed with more than one barrel configured as the first barrel or as the second barrel. For example, the dampening element 100 may be configured with two or more "first" barrels each configured to actively dampen pressure fluctuations of the pulsatile fluid flow in the distal direction (e.g., positive flow; during infusion). Each of the "first" barrels may be configured with a different biasing force (e.g., spring constant, etc.) to provide a desired responsiveness to the pulsatile fluid flow. Additionally or alternatively, the dampening element 100 may be configured with two or more "second" barrels each configured to actively dampen pressure fluctuations of the pulsatile fluid flow in the proximal direction (e.g., negative flow; during suction). Each of the "second" barrels may be configured with a different biasing force (e.g., spring constant, etc.) to provide a desired responsiveness to the pulsatile fluid flow. Varying combinations of multiple barrels are also contemplated.

Figure 14:
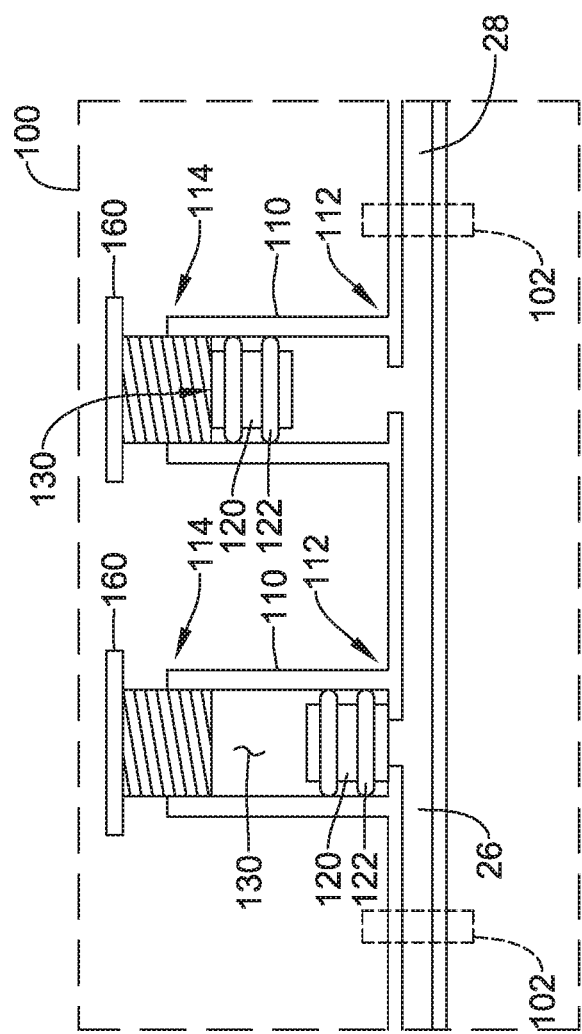

FIG. 14 illustrates a partial cross-sectional view of another example of the dampening element 100. The example illustrated in FIG. 14 combines selected features of the examples illustrated in FIGS. 5 and 6. However, it will be appreciated that the example of FIG. 14 may work equally well in and/or with features from any and/or all embodiments and/or examples of the dampening element 100 disclosed herein. Similarly, additional arrangements and/or combinations of features are also contemplated.

The dampening element 100 may be positioned and/or disposed between the first segment 26 of the fluid pathway and the second segment 28 of the fluid pathway. The dampening element 100 may be in fluid communication with the fluid pathway, and in some instances the dampening element 100 may be provided as a disposable tubing set with tubing extending from the dampening element 100 defining the first segment 26 and/or the second segment 28, which may be removably engaged with the fluid pump 20 for moving fluid therethrough. The dampening element 100 may comprise a plurality of barrels 110, each barrel 110 including a movable seal member 120 disposed within the barrel 110 (and/or a lumen defined by the barrel 110), a biasing member 130 disposed within the barrel 110 (and/or the lumen defined by the barrel 110) and engaged with the movable seal member 120, and a cap 140 (not shown in FIG. 14) secured to the barrel 110 opposite the fluid pathway. The cap 140 may be selectively lockable onto the barrel 110. Alternatively, some of and/or each barrel 110 may comprise an adjustable cap 160 as described herein.

In the example illustrated in FIG. 14, the plurality of barrels 110 may include and/or comprise a first barrel 110 and a second barrel 110. In at least some embodiments, the first barrel 110 and the second barrel 110 are both positioned between the fluid pump 20 and the fluid flow sensor 190 and/or the medical device 30. Other arrangements and/or configurations, including but not limited to three barrels, four barrels, five barrels, or more barrels, are also contemplated. The first barrel 110 may include a first movable seal member 120 disposed within the first barrel 110 (and/or the lumen defined by the first barrel 110) and a first biasing member 130 disposed within the first barrel 110 (and/or the lumen defined by the first barrel 110) and engaged with the first movable seal member 120. The second barrel 110 may include a second movable seal member 120 disposed within the second barrel 110 (and/or the lumen defined by the second barrel 110) and a second biasing member 130 disposed within the second barrel 110 (and/or the lumen defined by the second barrel 110) and engaged with the second movable seal member 120. In some embodiments, the first barrel 110 and the second barrel 110 may be formed as a unified housing. In some embodiments, the first barrel 110 may be structurally and/or functionally independent of the second barrel 110. As such, multiple first barrels and/or multiple second barrels may be utilized and/or included within the dampening element 100. In some embodiments, the fluid volume(s) desired to be accommodated by the one or more barrels 110 may be divided into several barrels placed in series with each other, thereby providing an additive configuration capable of accommodating a greater volume of fluid and/or a higher pressure pulse.

In should be noted that the orientation of the first barrel 110 and the second barrel 110 relative to each other and/or relative to the fluid pathway may be varied while maintaining the desired function(s) and/or benefits of the dampening element 100. In the view illustrated, the first barrel 110 and the second barrel 110 both extend upward from the fluid pathway and/or the first segment 26 and the second segment 28. In some embodiments, one of the first barrel 110 or the second barrel 110 may extend upward from the fluid pathway and/or the first segment 26 and the second segment 28 and the other of the first barrel 110 or the second barrel 110 may extend downward from the fluid pathway and/or the first segment 26 and the second segment 28. Alternatively, one of the first barrel 110 or the second barrel 110 may extend at a non-zero angle (e.g., 30 degrees, 45 degrees, 60 degrees, 90 degrees, 120 degrees, 150 degrees, etc.) relative to the other of the first barrel 110 or the second barrel 110. Other arrangements and/or configurations are also contemplated. For example, in some embodiments, positioning of the first barrel 110 and the second barrel 110 may be interchanged while retaining their respective functions. In some embodiments, the dampening element 100, the first barrel 110, and/or the second barrel 110 may be positioned in any orientation relative to the fluid pathway and/or the first segment 26 and the second segment 28 while retaining its respective function(s). For example, the dampening element 100, the first barrel 110, and/or the second barrel 110 may be positioned on its side, upside down, etc. This arrangement is equally applicable to all other embodiments described and contemplated within the context of this application.

The example illustrated in FIG. 14 includes adjustable caps 160, but this is not intended to be limiting, and the cap 140 and/or the adjustable cap 160 may be used in varying combinations as described herein. Additionally, as mentioned above, in some embodiments, the dampening element 100 may include the first connector 102 and/or the second connector 102 and/or multiples thereof.

In some embodiments, a first end 112 of each of the one or more barrels 110 (and/or each of the lumens defined by the one or more barrels 110) may include a port in fluid communication with the fluid pathway, and the cap 140 and/or the adjustable cap 160 may be secured to an opposing second end 114 of the barrel 110 (and/or the lumen defined by the barrel 110). The movable seal member 120 may be disposed within the barrel 110 (and/or the lumen defined by the barrel 110) between the port leading to the fluid pathway and the cap 140 and/or the adjustable cap 160. The movable seal member 120 may be configured to sealingly engage an inner surface and/or an inner wall of the barrel 110. In some embodiments, the movable seal member 120 may include at least one sealing element 122 extending around a perimeter of the movable seal member 120 and configured to sealingly engage the inner surface and/or the inner wall of the barrel 110. For example, in some embodiments, the at least one sealing element 122 may include at least one O-ring (e.g., one O-ring, two O-rings, three O-rings, etc.) extending around the movable seal member 120 and configured to sealingly engage the inner surface and/or the inner wall of the barrel 110.

The movable seal member 120 may be configured to translate axially within the one or more barrels 110 and/or within the lumen defined by the one or more barrels 110. In some embodiments, using two or more sealing elements 122 may help to prevent tilting, cocking, and/or wedging of the movable seal member 120 within the barrel 110 and/or the lumen defined by the barrel 110. The dampening element 100 may be configured to be responsive to pressure fluctuations of the pulsatile fluid flow to actively dampen the pressure fluctuations and smoothen the pulsatile fluid flow. In the example of FIG. 14, the biasing member 130 may be a trapped gas and/or a vacuum or partial vacuum trapped within the barrel 110 and/or the lumen defined by the barrel 110. In some embodiments, the trapped gas may be a compressed gas (i.e., a gas at a pressure greater than 14.7 psi) or a gas at atmospheric pressure (14.7 psi), such as atmospheric air. In the example of FIG. 14, the biasing member 130 (i.e., the trapped gas) may be disposed in within the barrel 110 between the movable seal member 120 and the cap 140.

Accordingly, the dampening element 100 may be configured to actively dampen pressure fluctuations of the pulsatile fluid flow in the distal direction (e.g., positive flow; during infusion). The first biasing member 130 may bias and/or urge the first movable seal member 120 toward and/or into an initial position proximate the first end 112. The first movable seal member 120, in the initial position, may be at the first end 112 of the barrel 110 immediately adjacent to the port of the first barrel 110 in fluid communication with the fluid pathway and/or the first segment 26 and/or the second segment 28. The first dampening element 100 may function similar to the dampening element 100 of FIG. 5 to be responsive to pressure fluctuations of the pulsatile fluid flow in a distal direction (e.g., positive pressure) to actively dampen the pressure fluctuations and smoothen the pulsatile fluid flow.

Furthermore, the second biasing member 130 may be a gas at atmospheric pressure (14.7 psi), such as atmospheric air, or a vacuum or a partial vacuum trapped within the second barrel 110 and/or the lumen defined by the second barrel 110. In the example of FIG. 14, the second biasing member 130 may be disposed within the second barrel 110 between the second movable seal member 120 and the cap 140 and/or the adjustable cap 160. Accordingly, the dampening element 100 may be configured to actively dampen pressure fluctuations of the pulsatile fluid flow in the proximal direction (e.g., negative flow; during suction). The second biasing member 130 may bias and/or urge the second movable seal member 120 toward and/or into an initial position proximate the second end 114. The second movable seal member 120, in the initial position, may be at the second end 114 of the second barrel 110 immediately adjacent to and/or in contact with the cap 140 and/or the adjustable cap 160. The second dampening element 100 may function similar to the dampening element 100 of FIG. 6 to be responsive to pressure fluctuations of the pulsatile fluid flow in a proximal direction (e.g., negative pressure) to actively dampen the pressure fluctuations and smoothen the pulsatile fluid flow.

In addition or alternatively, the dampening element 100 may be constructed with more than one barrel configured as the first barrel or as the second barrel. For example, the dampening element 100 may be configured with two or more "first" barrels each configured to actively dampen pressure fluctuations of the pulsatile fluid flow in the distal direction (e.g., positive flow; during infusion). Each of the "first" barrels may be configured with a different biasing force (e.g., gas pressure, etc.) to provide a desired responsiveness to the pulsatile fluid flow. Additionally or alternatively, the dampening element 100 may be configured with two or more "second" barrels each configured to actively dampen pressure fluctuations of the pulsatile fluid flow in the proximal direction (e.g., negative flow; during suction). Each of the "second" barrels may be configured with a different biasing force (e.g., gas or vacuum pressure, etc.) to provide a desired responsiveness to the pulsatile fluid flow. Varying combinations of multiple barrels are also contemplated.

As may be readily appreciated, while not explicitly illustrated, combinations of the configurations and/or features shown in FIGS. 13 and 14 are also contemplated, including but not limited to multiple barrels configured as the first barrel and/or the second barrel, as well as configurations of the first barrel and/or the second barrel including different types of biasing members (e.g., elastic element, gas, vacuum, etc.).

Figure 15:
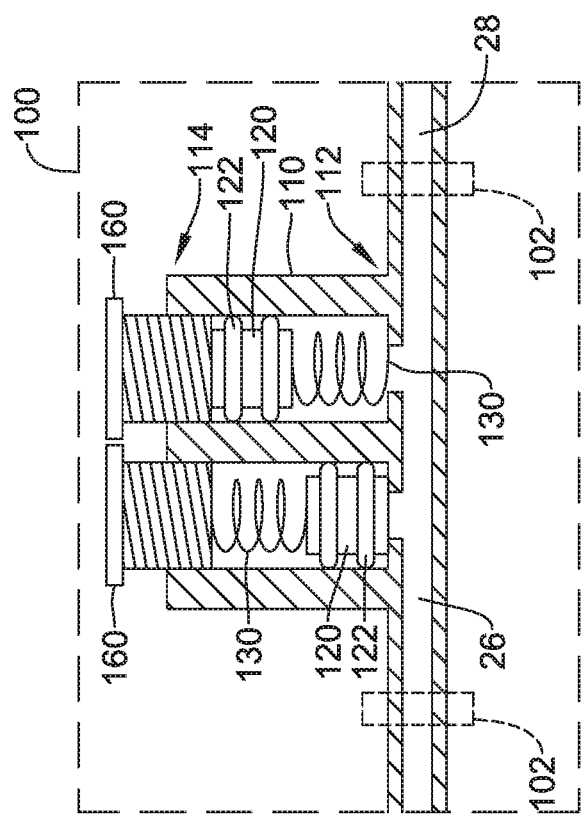
FIG. 15 illustrates an alternative configuration of an example dampening element.

FIG. 15 illustrates a partial cross-sectional view of another example of the dampening element 100. The example illustrated in FIG. 15 combines selected features of the examples illustrated in FIGS. 3 and 4. However, it will be appreciated that the example of FIG. 15 may work equally well in and/or with features from any and/or all embodiments and/or examples of the dampening element 100 disclosed herein. For example, in some embodiments, the example of FIG. 15 may be constructed using selected features of the examples illustrated in FIGS. 5 and 6. Similarly, additional arrangements and/or combinations of features are also contemplated.

Compared to FIGS. 3, 4, and 13 above, the example of FIG. 15 includes one or more barrels 110 formed as and/or within a single monolithic structure or housing. In some embodiments, the first barrel 110 and the second barrel 110 are formed as and/or within a single monolithic structure or housing. In some embodiments, the single monolithic structure may include two "first" barrels or two "second" barrels. Embodiments including additional barrels formed as and/or within the single monolithic structure are also contemplated.

Furthermore, in some embodiments, the dampening element 100 may include multiple instances of one or more barrels 110 being formed as and/or within a single monolithic structure. For example, the dampening element 100 may include two or more monolithic structures joined together using connectors 102. In some embodiments, the dampening element 100 may include one monolithic structure including two or more "first" barrels, and one monolithic structure including two or more "second" barrels coupled together along the fluid pathway. Other arrangements and/or configurations are also contemplated.

The materials that can be used for the various components of the fluid management system, the dampening element, the connectors, the one or more barrels, the movable seal member, the biasing member, the cap and/or the adjustable cap, the fluid flow sensor, etc. (and/or other systems or components disclosed herein) and the various elements thereof disclosed herein may include those commonly associated with medical devices. In some embodiments, the fluid management system, the dampening element, the connectors, the one or more barrels, the movable seal member, the biasing member, the cap and/or the adjustable cap, the fluid flow sensor, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, mild steel, nickel-titanium alloy such as linear-elastic and/or super-elastic nitinol, or any other suitable materials. Some examples of suitable polymers may include polytetrafluoroethylene (PTFE), ethylene tetrafluoroethylene (ETFE), fluorinated ethylene propylene (FEP), polyoxymethylene (POM), polyether block ester, polyurethane, polypropylene (PP), polyvinylchloride (PVC), polyether-ester, polyamide, polyether block amide (PEBA), ethylene vinyl acetate copolymers (EVA), silicones, polyethylene (PE), and other suitable materials.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A fluid management system, comprising:
    a fluid pump capable of generating a pulsatile flow of fluid;
    a fluid pathway for transporting the pulsatile flow of fluid from a fluid source through the fluid pump to a medical device;
    a dampening element in fluid communication with the fluid pathway, the dampening element comprising a first barrel and a second barrel each having a first end with a port in fluid communication with the fluid pathway and an opposing second end, the dampening element being responsive to pressure fluctuations of the pulsatile fluid flow to actively dampen the pressure fluctuations and smoothen the pulsatile fluid flow in both flow directions of the fluid pathway;
    wherein the first barrel includes a first movable seal member disposed within the first barrel, a first biasing member disposed within the first barrel and engaged with the first movable seal member, and a first cap secured to the second end of the first barrel, wherein the first biasing member is disposed between the first movable seal member and the first cap; and
    wherein the second barrel includes a second movable seal member disposed within the second barrel, a second biasing member disposed within the second barrel and engaged with the second movable seal member, and a second cap secured to the second end of the second barrel, wherein the second biasing member is disposed between the second movable seal member and the first end of the second barrel.

2. The fluid management system of claim 1, wherein the first barrel dampens the pulsatile fluid flow in a distal direction of the fluid pathway.

3. The fluid management system of claim 1, wherein the second barrel dampens the pulsatile fluid flow in a proximal direction of the fluid pathway.

4. The fluid management system of claim 1, wherein the first barrel is independent of the second barrel.

5. The fluid management system of claim 1, wherein the first barrel and the second barrel are formed within a single monolithic structure.

6. The fluid management system of claim 1, wherein the first barrel includes a cylindrical lumen; and
wherein the first movable seal member has a disk-like structure comprising at least one sealing element extending around a perimeter of the disk-like structure;
wherein the at least one sealing element is configured to sealingly engage an inner surface of the cylindrical lumen.

7. The fluid management system of claim 6, wherein the at least one sealing element comprises two or more O-rings.

8. The fluid management system of claim 6, wherein the first biasing member is a spring.

9. The fluid management system of claim 6, wherein the first biasing member is configured to translate an entirety of the first movable seal member along the inner surface of the cylindrical lumen in response to the pressure fluctuations of the pulsatile fluid flow.

10. The fluid management system of claim 1, wherein the second barrel includes a cylindrical lumen; and
wherein the second movable seal member has a disk-like structure comprising at least one sealing element extending around a perimeter of the disk-like structure;
wherein the at least one sealing element is configured to sealingly engage an inner surface of the cylindrical lumen.

11. The fluid management system of claim 10, wherein the at least one sealing element comprises two or more O-rings.

12. The fluid management system of claim 10, wherein the second biasing member is a spring.

13. The fluid management system of claim 10, wherein the second biasing member is configured to translate an entirety of the second movable seal member along the inner surface of the cylindrical lumen in response to the pressure fluctuations of the pulsatile fluid flow.

14. A fluid management system, comprising:
a fluid pump capable of generating a pulsatile flow of fluid;
a fluid pathway for transporting the pulsatile flow of fluid from a fluid source through the fluid pump to a medical device;
a dampening element in fluid communication with the fluid pathway, the dampening element comprising a first barrel and a second barrel each having a first end with a port in fluid communication with the fluid pathway and an opposing second end, the dampening element being responsive to pressure fluctuations of the pulsatile fluid flow to actively dampen the pressure fluctuations and smoothen the pulsatile fluid flow; and
a fluid flow sensor disposed along the fluid pathway between the dampening element and the medical device to measure a flow rate of the pulsatile fluid flow in both flow directions of the fluid pathway;
wherein the first barrel includes a first movable seal member disposed within the first barrel, a first biasing member disposed within the first barrel and engaged with the first movable seal member, and a first cap secured to the second end of the first barrel, wherein the first biasing member is disposed between the first movable seal member and the first cap, the first barrel being configured to dampen the pressure fluctuations in a distal direction of the fluid pathway;
wherein the second barrel includes a second movable seal member disposed within the second barrel, a second biasing member disposed within the second barrel and engaged with the second movable seal member, and a second cap secured to the second end of the second barrel, wherein the second biasing member is disposed between the second movable seal member and the first end of the second barrel, the second barrel being configured to dampen the pressure fluctuations in a proximal direction of the fluid pathway;
wherein the first barrel and the second barrel are both positioned between the fluid pump and the fluid flow sensor.

15. The fluid management system of claim 14, wherein the first biasing member is a spring.

16. The fluid management system of claim 15, wherein the spring is in compression.

17. The fluid management system of claim 14, wherein the second biasing member is a spring.

18. The fluid management system of claim 17, wherein the spring is in tension.

19. The fluid management system of claim 14, wherein the first biasing member is configured to move the first movable seal member along an inner surface of the first barrel in response to the pressure fluctuations of the pulsatile fluid flow.

20. The fluid management system of claim 14, wherein the second biasing member is configured to move the second movable seal member along an inner surface of the second barrel in response to the pressure fluctuations of the pulsatile fluid flow.

* * * * *